US006191154B1

United States Patent
Landreth et al.

(12)
(10) Patent No.: US 6,191,154 B1
(45) Date of Patent: Feb. 20, 2001

(54) COMPOSITIONS AND METHODS FOR THE TREATMENT OF ALZHEIMER'S DISEASE, CENTRAL NERVOUS SYSTEM INJURY, AND INFLAMMATORY DISEASES

(75) Inventors: Gary Landreth, Shaker Heights; Colin Combs, University Heights; Jerry Silver, Bay Village; Michael T. Fitch, S. Euclid, all of OH (US)

(73) Assignee: Case Western Reserve University, Cleveland, OH (US)

( * ) Notice: Under 35 U.S.C. 154(b), the term of this patent shall be extended for 0 days.

(21) Appl. No.: 09/200,700

(22) Filed: Nov. 27, 1998

(51) Int. Cl.[7] .................................................. A61K 31/425

(52) U.S. Cl. ........................ 514/369; 365/372; 365/367

(58) Field of Search ........................ 514/367, 369–372, 514/365

(56) References Cited

U.S. PATENT DOCUMENTS

| 4,287,200 | 9/1981 | Kawamatsu et al. | 514/369 |
|---|---|---|---|
| 4,340,605 | 7/1982 | Kawamatsu et al. | 514/342 |
| 4,376,777 | 3/1983 | Kawamatsu et al. | 514/369 |
| 4,438,141 | 3/1984 | Kawamatsu et al. | 514/236.8 |
| 4,444,779 | 4/1984 | Kawamatsu et al. | 514/342 |
| 4,461,902 | 7/1984 | Kawamatsu et al. | 548/183 |
| 4,572,912 | 2/1986 | Yoshioka et al. | 514/369 |
| 4,683,195 | 7/1987 | Mullis et al. | 435/6 |
| 4,683,202 | 7/1987 | Mullis | 435/91.2 |
| 4,687,777 | 8/1987 | Meguro et al. | 514/342 |
| 4,703,052 | 10/1987 | Eggler et al. | 514/337 |
| 4,725,610 | 2/1988 | Meguro et al. | 514/369 |
| 4,873,191 | 10/1989 | Wagner et al. | 800/25 |
| 4,873,255 | 10/1989 | Yoshioka et al. | 514/369 |
| 4,897,393 | 1/1990 | Iijima et al. | 514/233.8 |
| 4,897,405 | 1/1990 | Alessi et al. | 514/360 |
| 4,918,091 | 4/1990 | Cantello et al. | 514/369 |
| 4,948,900 | 8/1990 | Iijima et al. | 548/183 |
| 4,965,188 | 10/1990 | Mullis et al. | 435/6 |
| 5,002,953 | 3/1991 | Hindley | 514/275 |

(List continued on next page.)

FOREIGN PATENT DOCUMENTS

| WO89/08651 | 9/1989 | (WO) . |
|---|---|---|
| WO90/08832 | 8/1990 | (WO) . |
| WO91/07107 | 5/1991 | (WO) . |
| WO92/02520 | 2/1992 | (WO) . |
| WO94/04133 | 3/1994 | (WO) . |
| WO96/33724 | 10/1996 | (WO) . |

OTHER PUBLICATIONS

Anderson and Young, Quantitative Filter Hybridization, in *Nucleic Acid Hybridization* (1985) (printed copy of reference not available; will provide at a later date should the Examiner request it).

Antonucci et al., "Impaired Glucose Tolerance is Normalized by Treatment With the Thiazolidinedione Troglitazone," Diabetes Care 20:188 (1997).

Ausubel, *Current Protocols in Molecular Biology*, Wiley & Sons, New York (1994).

Balentine, "Pathology of Experimental Spinal Cord Trauma I. The Necrotic Lesion as a Function of Vascular Injury," Lab. Invest. 39:236 (1978).

Banati et al., "Cytotoxicity of Microglia," Glia 7:111 (1993).

Basso et al., "Graded Histological and Locomotor Outcomes after Spinal Cord Contusion Using the NYU Weight–Drop Device versus Transection," Exp. Neurol. 139:244 (1996).

(List continued on next page.)

Primary Examiner—Theodore J. Criares
(74) Attorney, Agent, or Firm—Medlen & Carroll, LLP

(57) ABSTRACT

The present invention relates to methods and compositions for treating Alzheimer's disease and other diseases and conditions with an inflammatory component (e.g., central nervous system injury). In particular, the present invention provides agents that regulate the production of proinflammatory and neurotoxic products involved in Alzheimer's disease and other diseases and conditions with an inflammatory component.

18 Claims, 22 Drawing Sheets

U.S. PATENT DOCUMENTS

| | | | |
|---|---|---|---|
| 5,061,717 | 10/1991 | Clark et al. | 514/342 |
| 5,120,754 | 6/1992 | Clark et al. | 514/369 |
| 5,132,317 | 7/1992 | Cantello et al. | 514/369 |
| 5,143,929 | 9/1992 | Belliotti et al. | 514/369 |
| 5,194,443 | 3/1993 | Hindley | 514/367 |
| 5,208,250 | 5/1993 | Cetenko et al. | 514/369 |
| 5,223,522 | 6/1993 | Clark et al. | 514/369 |
| 5,232,925 | 8/1993 | Hindley et al. | 514/272 |
| 5,260,445 | 11/1993 | Hindley | 548/183 |
| 5,270,319 | 12/1993 | Belliotti et al. | 514/269 |
| 5,326,770 * | 7/1994 | Wilkerson | 514/314 |
| 5,494,927 | 2/1996 | Cetenko et al. | 514/386 |
| 5,543,297 | 8/1996 | Cromlish et al. | 435/25 |
| 5,614,541 | 3/1997 | Backstrom et al. | 514/369 |
| 5,618,835 | 4/1997 | Wu et al. | 514/422 |
| 5,700,820 | 12/1997 | Vyas et al. | 514/369 |
| 5,714,470 | 2/1998 | Peet et al. | 514/17 |
| 5,814,647 | 9/1998 | Urban et al. | 514/369 |
| 5,824,692 | 10/1998 | Lippiello et al. | 514/343 |

OTHER PUBLICATIONS

Bauer et al., "Expression and retulation of cyclooxytenase–2 in rat microglia," Eur. J. Biochem. 243:726 (1997).

Beaudet, "Bibliography of cloned Human and Other Selected DNAs," Am. J. Hum. Gen. 37:386 (1985).

Berge et al., "Pharmaceutical Salts," J. Pharm. Science 66:1 (1997).

Berton and Gordon, "Modulation of macrophage mannosyl–specific receptors by cultivation on immobilized aymosan. Effects on superoxide–anion release and phagocytosis," Immunology 49:705 (1983).

Blight, "Effects of silica on the outcome from experimental spinal cord injury: implication of macrophages in secondary tissue damage," Neuroscience 60:263 (1994).

Borchelt et al., "Accelerated Amyloid Deposition in the Brains of Transgenic Mice Coexpressing Mutant Presenilin 1 and Amyloid Percursor Proteins," Neuron 19:939 (1997).

Boshart et al., "A Very Strong Enhancer is Located Upstream of an Immediate Early Gene of Human Cytomegalovirus," Cell 41:521–530 (1985).

Bradford, "A Rapid and Sensitive Method for the Quantitation of Microgram Quantities of Protein Utilizing the Principle of Protein–Dye Binding," Anal. Biochem. 72:248 (1976).

Bradley et al., "Formation of germ–line chimaeras from embryo–derived teratocarcinoma cell lines," Nature 309:255–258 (1984).

Brinster et al., "Factors affecting the efficienty of introducing foreing DNA into mice by microinjecting eggs," Proc. Natl. Acad. Sci. USA, 82:4438–4442 (1985).

Brown et al., "Role of microglia and host prion protein in neurotixicity of a prion protein fragment," Nature 380:345–347 (1996).

Burridge and Chrzanowska, "Focal adhesions, contractility, and signaling," Ann. Rev. Cell Dev. Biol. 12:463 (1996).

Camras et al., "Latanoprost, a Prostaglandin Analog, for Glaucoma Therapy: efficacy and Safety after 1 Year of Treatment in 198 Patients," Opthamology 103:1916–1924 (1996).

Chamberlain et al., "New RNA Polymerase from *Escherichia coli* infected with Bacteriophage T7," Nature 228:227–231 (1970).

Constantini and Young, "The effects of methylprednisolone and the ganglioside GM1 on acute spinal cord injury in rats," J. Neurosurg. 80:97 (1994).

Cotman et al., "β–Amyloid Converts an Acute Phase Injury Response to Chronic Injury Responses," Neurobiol. Aging 17:723 (1996).

Czop, "Phagocytosis of Particulate Activators of the Alternative Complement Pathsay: Effects of Fibronectin," Adv. Immunol. 38:361 (1986).

Daum and Rohrback, "Zymosan induces selective release of arachidonic acid from rabbit alveolar macrophages via stimulation of a β–glucan receptor," FEBS 309:110 (1992).

Dijkema et al., "Cloning and expression of the chromosomal immune interferon gene of the rat," EMBO J. 4:761–767 (1985).

Ducker et al., "Pathological findings inacute experimental spinal cord trauma," J. Neurosurg. 35:700 (1971).

Erlich (ed.), *PCR Technology*, Stockton Press, New York (1989).

Evans et al., "Establishment in culture of pluripotential cells from mouse embryos," Nature 292:154–56 (1981).

Fitch and Silver, "Activated Macrophages and the Blood––Brain Barrier: Inflammation after CNS Injury leads to Increased Putative Inhibitory Molecules," Exp. Neuro. 148:587 (1997).

Franzese et al., "Effect of prostaglandin $A_1$ on proliferation and telomerase activity of human melanoma cells in vitro," Melanoma Rs. 8:323 (1998).

Frautschy et al., "Microglial Response to Amyloid Plaques in APPsw Transgenic Mice," Am. J. Pathol. 152:307 (1998).

Fukumoto et al., "Association of Aβ40–positive Senile Plaques with Microglial Cells in the Brains of Patients with Alzheimer's Disease and in Non–demented Aged Individuals," Neurodegen. 5:13 (1996).

Gaupp et al., "Modulation of experimental autoimmune neuritis in Lewis rats by oral application of myelin antigens," J. Neuroimmunol. 79:129 (1997).

Ghazizadeh et al., "Physical and Functional Association of Src–related Protein Tyrosine Kinases with FcγRII in Monocytic ThP–1 Cells," J. Biol. Chem. 269:8878 (1994).

Ghazzi et al., "Cardiac and Glycemic Benefits of Troglitazone Treatment in NIDDM," Diabetes 46:433 (1997).

Giulian et al., "Phagocytic microglia release cytokines and cytotoxins that regulate the survival of astrocytes and neurons in culture," Neurochem. Int. 25:227 (1994).

Giulian et al., "Senile Plaques Stimulate Microglia to Release a Neurotoxin Found in Alzheimer Brain," Neurochem. Int. 27:119 (1995).

Giulian, "Reactive Glia as Rivals in Regulating Neuronal Survival," Glia 7:102 (1993).

Giulian et al., "The Role of Mononuclear Phagocytes in Would Healing After Traumatic Injury to Adult Mammalian Brain," Neurosci. 9:4416 (1989).

Guilian et al., "Specific Domains of β–Amyloid from Alzheimer Plaque Elicit Neuron Killing in Human Microglia," J. Neurosci. 16:6021 (1996).

Giulian et al., "The Impact of Microglia–Derived Cytokines upon Gliosis in the CNS," Dev. Neurosci. 6:128 (1994).

Giulian and Lachman, "Interleukin–1 Stimulation of Astroglial Proliferation After Brain Injury," Science 228:497 (1985).

Gorman et al., "The Rous sarcoma virus long terminal report is a strong promoter when introduced into a variety of eukaryotic cells by DNA–mediated transfection," Proc. Natl. Acad. Sci. USA 79:6777–6781 (1982).

Gossler et al., "Transgenesis by means of blastocyst–derived embryonic stem cell lines," Proc. Nat. Acad. Sci. USA 83:9065–9069 (1986).

Graham and Van der Eb, "A New Technique for the Assay of Infectivity of Human Adenovirus 5 DNA," Virol., 52:456–467 (1973).

Guth et al., "Essentiality of a Specific Cellular Terrain for Growth of Axons into a Spinal Cord Lesion," Exp. Neurol. 88:1 (1985).
pg,5

Guth et al., "Key role for pregnenolone in combination therapy that promotes recovery after spinal injury," Proc. Nat. Acad. Sci. 91:12308 (1994).

Guth et al., "Spinal Cord Injury in the Rat: Treatment with Bacterial Lipopolysaccharide and Indomethacin Enhances Cellular Repair and Locomotor Function," Exp. Neurol. 126:76 (1994).

Hashimoto et al., "Nitric Oxide Synthesis in Murine Peritoneal Macrophages by Fungal β–Gllucans," Biol. Pharm. Bull. 20:1006 (1997).

Haskell and Bowen, "Efficient Production of Transgenic Cattle by Retroviral Infection of Early Embryos," Mol. Reprod. Dev., 40:386–390 (1995).

Heun et al., "The Validity of Psychometric Instruments for Detection of dementia in the Elderly General Population," Int. J. Geriatr. Psychiatry 13:368 (1998).

Hillhouse et al., "Middle cerebral artery occlusion in the rat causes a biphasic production of immunoreactive interleukin–1β in the cerebral cortex," Neurosci. Lett. 249:177 (1997).

Ho et al., "Human autoimmune neuropathies," Ann. Rev. Neurosci. 21:187 (1998).

Hogan et al., *Manipulating the Mouse Embryo*, Cold Spring Harbor Laboratory Press, Cold Spring harbor, N.Y. (1986).

Hwang et al., "Expression of Mitogen–Inducible Cyclooxygenase Induced by Lipopolysaccharide: Mediation through both mitogen–activated protein kinase and NF–κB signaling pathways in macrophages," Biochem. Pharmacol. 54:87 (1997).

Ii et al., "β–Amyloid protein–dependent nitric oxide production from microglial cells and neurotoxicity," Brain Res. 720:93 (1996).

Inoue et al., "Transcriptional Regulation of Human Prostaglandin–endoperoxide Synthase–2 Gene by Lipopolysaccharide and Phorbol Ester in Vascular Endothelial Cells," J. Biol. Chem. 270:24965 (1995).

Itagaki et al., "Relationship of microglia and astrocytes to amyloid deposits of Alzheimer disease," J. Neuroimmunol. 24:173 (1989).

Iwamoto et al., "Effect of New oral Antidiabetic Agent CS–045 on Glucose Tolerance and insulin Secretion in Patients with NIDDM," Diabetes Care 14:1083 (1991).

Iwamoto et al., "Effects of Troglitazone: A new hypoglycemic agent in patients with NIDDM poorly controlled by diet therapy," Diabetes Care 19:151 (1996).

Jaenisch, "Germ line integration and Mendelian transmission of the exogenous Moloney lukemia virus," Proc. Nat. Acad. Sci. USA 73:1260–1264 (1976).

Jaenisch, "Transgenic Animals," Science 240:1468–1474 (1988).

Jahner et al., "Insertion of the bacterial gpt gene into the germ line of mice by retroviral infection," Proc. Nat. Acad. Sci. USA 82:6927–6931 (1985).

Jahner et al., "De novo methylation and expression of retroviral genomes during mouse embryogenesis," Nature 298:623–628 (1982).

Johnson et al., "Troglitazone: Review and Assessment of Its Role in the Treatment of Patients with Impaired Glucose Tolerance and Diabetes Mellitus," Ann. Pharma. 32:337 (1998).

Kacian et al., "A Replicating RNA Molecule Suitable for a Detailed Analysis of Extracellular Evolution and Replication," Proc. Nat. Acad. Sci USA 69:3038 (1972).

Kao et al., "The mechnaism of spinal cord cavitation following spinal cord transection," J. Neurosurg. 46:757 (1977).

Kaufmann et al., "Cyclooxygenases and the Central Nervous System," Prostaglandins 54:601 (1997).

Kiener et al., "Cross–linking of Fcγ RI) and Receptor II (FcγII) on Monocytic Cells Activates a Signal Transduction Pathway Common to Both Fc Receptors That Involves the Stimulation of p72 Syk Protein Tyrosine Kinase," J. Biol. Chem. 268:24442 (1993).

Kim et al., "Use of the human elongation factor 1α promoter as a versatile and efficient expression system," Gene 91:217–223 (1990).

Kretzschmar et al., "Cell death in prion disease," J. Neur. Trnasm. 50 (1997).

Lagenaur and Lemmon, "An L1–like molecule, the 8D9 antigen, is a potent substrate for neurite extension," Proc. Nat. Acad. Sci. 84:7753 (1987).

Lemberger et al., "Peroxisome proferator–activated receptors: A nuclear receptor signaling pathway in lipid physiology," Annu. Rev. Cell Dev. Biol. 12:335 (1996).

Lev et al., "Protein tyrosine kinase PYK2 involved in $Ca^{2+}$–induced regulation of ion channel and MAP kinase functions," Nature 376:737–745 (1995).

Loi et al., "Meta–Analysis of Steady–State Pharmacokinetics of Troglitazone and Its Metabolites," J. Clin. Pharmacol. 37:1038–1047 (1997).

Lombard et al., "A new method for studying the binding and ingestion of zymosan particles by macrophages," J. Immunol. Methods 174:155 (1994).

Maniatis et al., *Molecular Cloning, A Laboratory Manual* Cold Spring Harbor Laboratory Press, New York (1982).

Maniatis et al., "Regulation of Inducible and Tissue–Specific Gene Expression," Science 236:1237–1244 (1987).

Mann et al., "Microglial cells and amyloid β protein (Aβ) deposition: association with $Aβ_{40}$–containing plaques," Acta Neuropath. 90:472 (1995).

Martiney et al., "Prevention and Treatment of Experimental Autoimmune Encephalomyelitis by CN1–1493, a Macrophage–Deactivating Agent," J. Immunol. 160:5588 (1998).

Masliah et al., "Comparison of Neurodegenerative Pathology in Transgenic Mice Overexpressing V717F β–Amyloid Precursor Protein and Alzheimer's Disease," J. Neurosci. 16:5795 (1996).

McDonald et al., "β–Amyloid Fibrils Activate Parallel Mitogen–Activated Protein Kinase Pathways in Microglia and THP1 Monocytes," J. Neurosci. 18:4451–4460 (1997).

McGreer and Rogers, "Anti–inflammatory agents as a therapeutic approach to Alzheimer's disease," Neurology 42:447 (1992).

Means and Anderson, "Neuronophagia by Leukocytes in Experimental Spinal Cord Injury," J. Neuropath. Exp. Neurol. 42:707 (1983).

Miyazono et al., "A Comparative Immunohistoxhemical Study of Kuru and Senile Plaques with a Special reference to Glial Reactions at Various Stages of Amyloid Plaque Formation," Am. J. Path. 139:589 (1991).

Mizushima and Nagata, "pEF–BOS, a powerful mammalian expression vector," Nuc. Acids Res. 18:5322 (1990).

Nelson et al., "The effect of Dietary Docosahexaenoic Acid of Plasma Lipoproteins and Tissue Fatty Acid Composition in Humans," Lipids 32:1137 (1997).

Nolan et al., "Improvement in Glucose Tolerance and Insulin Resistence in Obese Subjects Treated with Troglitazone," N. Engl. J. Med. 331:1188 (1994).

Oakes et al., "The Insulin Sensitizer, BRL 49653, Reduces Systemic Fatty Acid Supply and Utilization and Tissue Lipid Availability in the Rat," Metabolism 46:935 (1997).

Ogihara et al., "Enhancement of Insulin Sensitivity by Troglitazone Lowers Blood Pressure in Diabetic Hypertensives," Am. J. Hypertens. 8:316 (1995).

Ofek et al. "Nonopsonic phagocytosis of miroorganisms," Annu. Rev. Microbiol. 49:239 (1995).

Perlmutter et al., "Morphologic association between microgla an senile plaque amyloid in Alzheimer's disease," Neurosci Lett. 119:32 (1990).

Remington's Pharmaceutical Sciences, E. W. Martin, ed., Mack Publishing Co, PA (1990).

Ricote et al., "The peroxisome proliferator–activated receptor–γ is a negative regulator of macrophage activation," Nature 391:79 (1998).

Robertson et al., "Germ–line transmission of genes introduced into cultured pluripotential cells by retroviral vector," Nature 322:445–48 (1986).

Rogers et al., "Donepezil Improves Cognition and Global Function in Alzheimer's Disease," Arch. Inten. Med. 58:1021 (1998).

Rothwell et al., "The Role of Interleukin 1 in Acute Neurodegeneration and Stroke: Pathophysiological and Therapeutic Impliations," J. Clin. Invest. 100:2648 (1998).

Saltiel and Olefsky, "Thiazolidinediones in the Treatment of Insulin Resistance and Type II Diabetes," Diabetes 45:1661 (1996).

Sambrook et al., Molecular Cloning: A Laboratory Manual, 2nd Ed., Cold Spring Harbor Laboratory Press, New York (1989) p. 6.9–6.15; 16.7–16.8.

Sano et al., "A controlled trial of selegiline, alpha–tocopherol, or both as treatment of Alzheimer's disease," New Engl. J. Med. 336:1216 (1997).

Scrammell et al., "Activation of ventrolateral preoptic neurons by the somnogen prostaglandin $D_2$," Proc. Nat. Acad. Sci. 95:7754 (1998).

pg,7

Sharma and Kumar, "Role of Proinflammatory Cytikines in Cerebral Ischemia: a Review," Met. Brain Dis. 13:1–8 (1998).

Smith et al., "Prostaglandin Enderperoxide H Synthases (Cyclooxygenases)–1 and –2," J. Biol. Chem. 271:33157 (1996).

Stewart et al., "Expression of retroviral vetors in transgenic mice obtained by embryo infection," EMBO J. 6:383–388 (1987).

Stewart and Weir, "Carbohydrates as recognition molecules in macrophage activities," J. Clin. Lab. Immunol. 28:103 (1989).

Sturchler–Pierrat et al., "Two amyloid precursor protein transgenic mouse models with Alzheimer disease–like pathology," Proc. Natl. Acad. Sci. 94:13287 (1997).

Suter et al., "Metabolic Effects of New Oral Hypoglycemic Agent CS–045 in NIDDM Subjects," Diabetes Care 15:193 (1992).

Szczepanik et al., "Effects of chronic intrahippocampal infusion of lipopolysaccharide in the rat," Neuroscience 70:57 (1996).

Tapper and Sundler, "Glucan receptor and zymosan–induced lysosomal enzyme secretion in macrophages," Biochem. J. 306:829 (1995).

Tsai and Wiltbank, "Prostaglandin $F_{2\alpha}$ Induces expression of Prostaglandin G/H Synthase–2 in the Ovine Corpus Luteum: A Potential Positive Feedback Loop during Luteolysis," Biol. Reprod. 57:1016 (1997).

Tsuchiya et al., "Induction of Maturation in Cultured Human Monocytic Leukemia Cells by a Phorbol Ester," Cancer Res. 42:1530 (1982).

Uetsuki et al., "Isolation and characterization of the Human Chromosomal Gene for Polypeptide Chain Elongation Factor–1α," J. Biol. Chem. 264:5791 (1989).

Van der Putten et al., "Efficient insertions of genes into the mouse germ line via retroviral vectors," Proc. Nat. Acad. Sci. USA 82:6148 (1985).

Vane et al., "Cyclooxygenases 1 and 2," Ann. Rev. Pharm. Tox. 38:97 (1998).

Voss et al., "The role of enhancers in the regulation of cell–type–specific transcriptional control," Trends Biochem. Sci. 11:287–289 (1986).

Wallace et al., "Chronic Regenerative Changes in the Spinal Cord after Cord Compression Injury in Rats," Surg. Neurol. 27:209 (1987).

Wang et al., "Increased feeding in fatty Zucker rats by the thiazolidinedione BRL 49653 (rosiglitazone) and the possible involvement of leptin and hypothalamic neuropeptide Y," Br. J. Pharmacol. 122:1405 (1997).

Weldon et al., "Fibrillar β–Amyloid Induces Microglial Phagocytosis, Expression of Inducible Nitric Oxide Synthase, and Loss of a Select Population of Neurons in the Rat CNS In Vivo," J. Neurosci. 18:2161 (1998).

Wu, "Endothelial Prostaglandin and Nitric Oxide Synthesis in Atherogenesis and Thrombosis," J. Formos, Med. Assoc. 95:661–666 (1996).

Wu and Wallace, "The Ligation Amplification Reaction (LAR)—Amplification of Specific DNA Sequences Using Sequential Rounds of Template–Dependent Ligation," Genomics 4:560 (1989).

Yamanoto et al., "Transcriptional Roles of Nuclear Fator κB and Nuclear Factor–Interleukin–6 in the Tumor Necrosis Factor α–Dependent Induction of Cyclooxygenase–2 in MC3T3–E1 Cells," J. Biol. Chem. 270:31315 (1995).

Zhang et al., "Experimental Analysis of Progressive Necrosis after Spinal Cord Trauma in the Rat: Etiological Role of the Inflammatory Response," Exp. Neuro 143:141 (1997).

Zhu et al., "Cytokine production and the pathogenesis of experimental autoimmune neuritis and Guillain–Barré syndrome," J. Neuroimmunol. 84:40 (1998).

McDonald et al., "Amyloid Fibrils Activate Tyrosine Kinase–Dependent Signaling and Superoxide Production in Microglia," J. Neurosci. 17:2284–2294 (1997).

Rogers et al., "Inflammation and Alzheimer's Disease Pathogenesis," Neurobiol. Aging 17:681–686 (1996).

Rich et al., "Nonsteroidal anti–inflammatory drugs in alzheimer's disease," Neurology 45:51–54 (1995).

Stewart et al., "Risk of Alzheimer's disease and duration of NSAID use," Neurology 48:626–632 (1997).

Coombs et al., "Inflammatory Mechanisms in Alzheimer's Disease: Inhibition of β–Amyloid–Stimulated Proinflammatory Responses and Neurotoxicity by PPARγ Agonists," (slated for publication in Jan. 2000).

Fitch et al., "Cellular and Molecular Mechanisms of Glial Scarring and Progressive Cavitation: In Vivo and In Vitro Analysis of Inflammation–Induced Secondary Injury after CNS Trauma," J. Neurosci. 19:8182–8198 (1999).

* cited by examiner

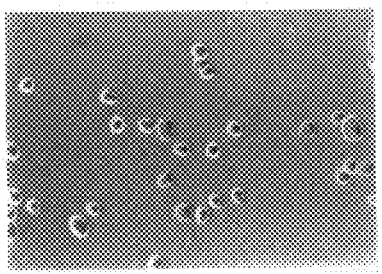
FIG. 3A control
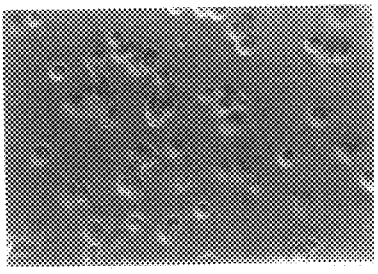
FIG. 3B 100nM TPA
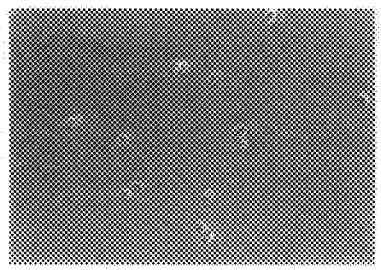
FIG. 3C 10µM PGJ2
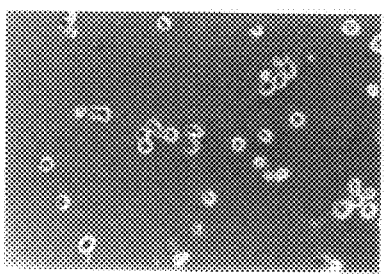
FIG. 3D 100nM TPA 10µM PGJ2

50µM Ciglitizone

100nM TPA
50µM Ciglitizone

50µM Troglitazone

100nM TPA
50µM Troglitazone

FIG. 4A control 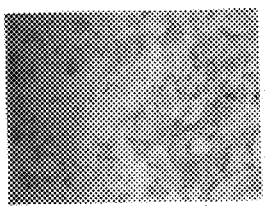
FIG. 4B 8A/THP-1 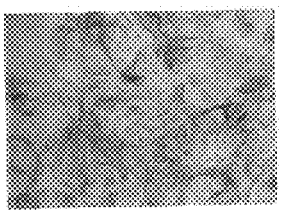
FIG. 4C A/THP-1/10µM PGJ2 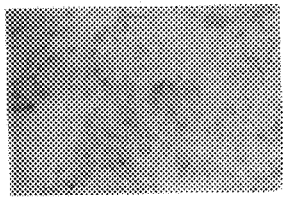
FIG. 4D 10µM PGJ2 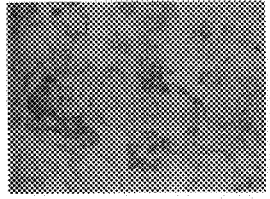
FIG. 4E 8A 25-35 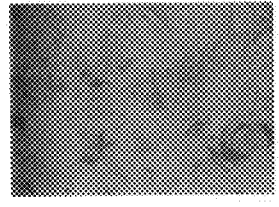
FIG. 4F THP-1 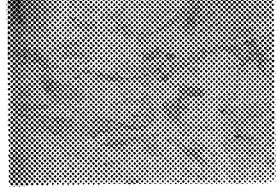

TPA (100 nM)  -  -  +  +  +  +  +  +
PGJ2 (μM)  -  -  -  0.5  1  2  5  10

LPS (25 μg)  -  -  -  +  +  +  +  +  +
PGJ2 (μM)  -  -  -  -  0.5  1  2  5  10

FORMULA IX
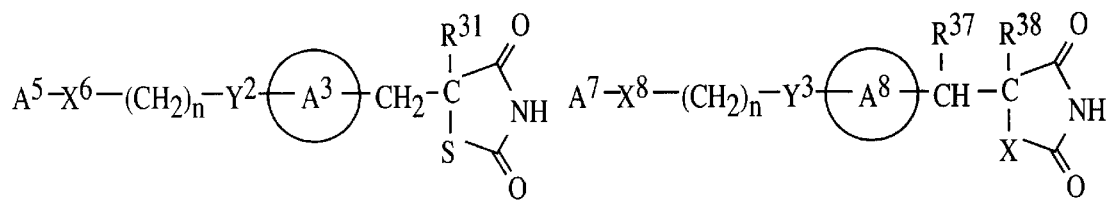
FORMULA X
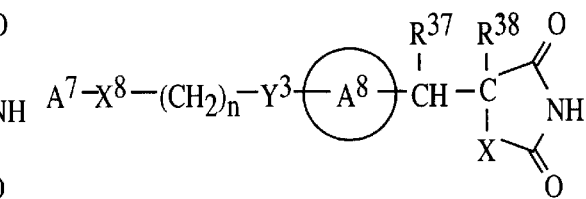
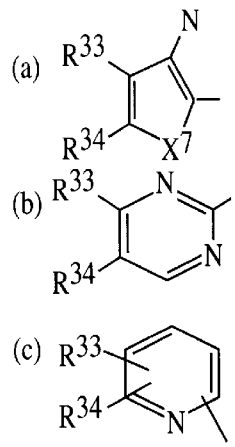
FORMULA (d)
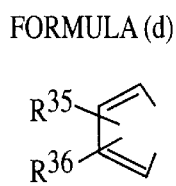
FORMULA XI
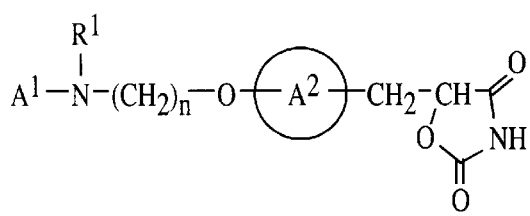
FORMULA XII
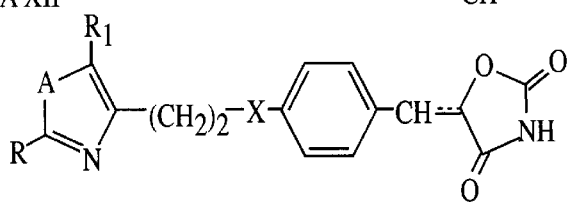
FORMULA XIII
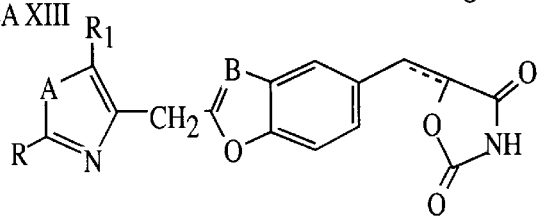
FIG. 15C

```
   1 ctcgatcaaa ccttttttt  atggtacaca atagtcacag tacttttcca tataaaacag
  61 gtttagtggt cttaatttag tttggcacat ttaatacact cccatgacca gcatcccaaa
 121 tgtacctatc cgttttattt tattgtctca gaattgtcag ttatttaata aattatgtaa
 181 cttttttcct tatgctcaga tttgcacttc tttctaaaac tctgcccatc cttaaagtcc
 241 cagattctcc ttgaactttt ttttttgact ttccaagtac atggaactct tcactctatc
 301 ctgctatata aggtgacaga atttccacta tgggatagat ggagttcaat tcctttgagt
 361 ttaaaataat ctaaatataa ttattcctta tgccctgttt ttccctcact tttgtatcca
 421 aatctctttt cagacaacag aacaattaat gtctgataag gaagacaatg atgatgatca
 481 cttcaaaatg aattcaggat tgtaatgtaa aatttttagta ctctctcaca gtatggattc
 541 taacatggct tctaacccaa actaacatta gtagctctaa ctataaactt caaatttcag
 601 tagatgcaac ctactccttt aaaatgaaac agaagattga aattattaaa ttatcaaaaa
 661 gaaaatgatc cacgctctta gttgaaattt catgtaagat tccatgcaat aaataggagt
 721 gccataaatg gaatgatgaa atatgactag aggaggagaa aggctcctag atgagatggg
 781 attttaggca tccgtgtctc atgaggaatc agttgtgtca ctaggcaaaa cagtaaaaaa
 841 aaaaacctcc aagtgagtct cttatttatt tttttcttat aagacttcta caaattgagg
 901 tacctggtgt agttttattt caggttttat gctgtcattt tcctgtaatg ctaaggactt
 961 aggacataac tgaattttct attttccact tcttttctgg tgtgtgtgta tatatatatg
1021 tatatataca cacacacata tacatatata tattttttag tatctcaccc tcacatgctc
1081 ctccctgagc actacccatg atagatgtta aacaaaagca aagatgaaat tccaactgtc
1141 aaaatccccc ctccatctaa ttaatccctc acccaactat gttccaaaac gagaatagaa
1201 aattagcccc aataagccca ggcaactgaa aagtaaatgc tatgttgtac tttgatccat
1261 ggtcacaact cataatcttg gaaaagtgga cagaaaagac aaaagagtga actttaaaac
1321 tcgaatttat tttaccagta tctcctatga agggctagta accaaaataa tccacgcatc
1381 agggagagaa atgccttaag gcatacgttt tggacattta gcgtccctgc aaattctggc
1441 catcgccgct tcctttgtcc atcagaaggc aggaaacttt atattggtga cccgtggagc
1501 tcacattaac tatttacagg gtaactgctt aggaccagta ttatgaggag aatttacctt
1561 tcccgcctct cttccaaga aacaaggagg gggtgaaggt acggagaaca gtatttcttc
1621 tgttgaaagc aacttagcta caaagataaa ttacagctat gtacactgaa ggtagctatt
1681 tcattccaca aaataagagt tttttaaaaa gctatgtatg tatgtgctgc atatagagca
1741 gatatacagc ctattaagcg tcgtcactaa aacataaaac atgtcagcct ttcttaacct
1801 tactcgcccc agtctgtccc gacgtgactt cctcgaccct ctaaagacgt acagaccaga
1861 cacggcggcg gcggcgggag aggggattcc ctgcggcccc ggacctcagg gccgctcaga
1921 ttcctggaga ggaagccaag tgtccttctg ccctcccccg gtatcccatc caaggcgatc
1981 agtccacaac tggctctcgg aagcactcgg gcaaagactg cgaagaagaa aagacatctg
2041 gcggaaacct gtgcgcctgg ggcggtggaa ctcggggagg agagggaggg atcagacagg
2101 agagtgggga ctacccctc tgctcccaaa ttggggcagc ttcctgggtt tccgattttc
2161 tcatttccgt gggtaaaaaa ccctgccccc accggcttac gcaatttttt taaggggaga
2221 ggagggaaaa atttgtgggg ggtacgaaaa ggcggaaaga aacagtcatt tcgtcacatg
2281 ggcttggttt tcagtcttat aaaaaggaag gttctctcgg ttagcgacca attgtcatac
2341 gacttgcagt gagcgtcagg agcacgtcca ggaactcctc agcagcgcct ccttcagctc
```

FIG. 18

COMPOSITIONS AND METHODS FOR THE TREATMENT OF ALZHEIMER'S DISEASE, CENTRAL NERVOUS SYSTEM INJURY, AND INFLAMMATORY DISEASES

This invention was made in part during work partially supported by the U.S. National Institutes of Health, under grant number 1-PO1-AG08012. The government has certain rights in this invention.

FIELD OF THE INVENTION

The present invention relates to methods and compositions for treating Alzheimer's disease and other diseases and conditions with an inflammatory component (e.g., central nervous system injury). In particular, the present invention provides agents that regulate the production of proinflammatory and neurotoxic products involved in Alzheimer's disease and other inflammatory diseases.

BACKGROUND OF THE INVENTION

Alzheimer's disease (AD) is a complex multi-genic neurodegenerative disorder characterized by progressive impairments in memory, behavior, language, and visuospatial skills, ending ultimately in death. Hallmark pathologies within vulnerable regions include extracellular β-amyloid deposits, intracellular neurofibrillary tangles, synaptic loss, and extensive neuronal cell death. Research on the causes and treatments of Alzheimer's disease has led investigators down numerous avenues. Although many models have been proposed, no single model of AD satisfactorily accounts for all neuropathologic findings as well as the requirement of aging for disease onset. The mechanisms of disease progression are equally unclear. Considerable human genetic evidence has implicated alterations in production or processing of the human amyloid precursor protein (APP) in the etiology of the disease. However, intensive research has proven that AD is a multifactorial disease with many different, perhaps overlapping, etiologies.

To date, Alzheimer's disease is the third most expensive disease in the United States, costing society approximately $100 billion each year. It is one of the most prevalent illnesses in the elderly population, and with the aging of society, will become even more significant. Costs associated with AD include direct medical costs such as nursing home care, direct nonmedical costs such as in-home day care, and indirect costs such as lost patient and care giver productivity. Medical treatment may have economic benefits by slowing the rate of cognitive decline, delaying institutionalization, reducing care giver hours, and improving quality of life. Pharmacoeconomic evaluations have shown positive results regarding the effect of drug therapy on nursing home placement, cognition, and care giver time.

Thus far, the therapeutic strategies attempted have targeted neurotransmitter replacement, or the preservation of normal brain structures, which potentially provide short-time relief, but do not prevent neuronal degeneration and death. Thus, there is a need for therapies that prevent neuronal degeneration and death associated with Alzheimer's disease and provide long-term relief.

SUMMARY OF THE INVENTION

The present invention relates to methods and compositions for treating Alzheimer's disease and other diseases and conditions with an inflammatory component (e.g., central nervous system injury). In particular, the present invention provides agents that regulate the production of proinflammatory and neurotoxic products involved in Alzheimer's disease and other inflammatory diseases.

The present invention provides methods for treating a subject, comprising administering a therapeutically effective amount of a PPARγ agonist to the subject, wherein the subject is selected from the group consisting of subjects suffering from Alzheimer's disease and subjects susceptible to Alzheimer's disease.

The present invention also provides methods for treating a subject suffering from central nervous system injury, comprising administering a therapeutically effective amount of a PPARγ agonist to the subject suffering from central nervous system injury.

The present invention further provides methods for treating a subject, comprising administering a therapeutically effective amount of a PPARγ agonist to the subject, wherein the subject is selected from the group consisting of subjects suffering from a disease with an inflammatory component and subjects susceptible to a disease with an inflammatory component. In some embodiments, the disease with an inflammatory component is selected from the group consisting of Alzheimer's disease, stroke, traumatic injury, and spinal injury, although it is contemplated that the methods of the present invention find use in the treatment of any disease with an inflammatory component.

In some embodiments of the present invention, the PPARγ agonist comprises a thiazolidinedione, although all PPARγ ligands and regulatory factors are contemplated by the present invention. In some embodiments, the thiazolidinedione comprises, but is not limited to, troglitazone, ciglitazone, pioglitazone, BRL 49653, englitazone, or combinations thereof. In other embodiments, the PPARγ agonist comprises, but is not limited to, docosahexaenoic acid, prostaglandin $J_2$ and prostaglandin $J_2$ analogs (e.g., $^{12}$-prostaglandin $J_2$ and 15-deoxy-$\Delta^{12,14}$-prostaglandin $J_2$).

In some embodiments of the present invention, the administering comprises oral administering, although all administration means are contemplated. In some embodiments, the therapeutically effective amount of the PPARγ agonist comprises approximately 10 mg/kg per day, although greater or lessor amounts are contemplated by the present invention.

The present invention also provides methods for measuring the ability of a compound (e.g., agonists and antagonists) to modify PPARγ-mediated gene transcription of the cox-2 gene, comprising: providing one or more test compounds; and a host cell transfected with a DNA construct comprising an oligonucleotide sequence comprising, in operable order, 1) a PPARγ-sensitive cox-2 regulatory element 2) a promoter and 3) a heterologous gene; and contacting the one or more test compounds with the host cell under conditions in which expression of the heterologous gene is responsive to the one or more compounds. In some embodiments, the method further comprises the step of comparing the level of gene expression of the heterologous gene in step b) with the level of gene expression from the host cell in the absence of the one or more compounds. In one preferred embodiment of the present invention, the DNA construct comprising an oligonucleotide sequence comprising a PPARγ-sensitive cox-2 regulatory element comprises SEQ ID NO:1.

The present invention further provides a method for regulating COX-2 expression, comprising: providing one or more cells expressing COX-2; means for expressing PPARγ in the one or more cells; and one or more PPARγ agonists; and introducing into the one or more cells, in any order, the means for expressing PPARγ and the one or more PPARγ agonists. In some embodiment, the one or more cells expressing COX-2 comprise cell that express an abnormal level of COX-2.

DESCRIPTION OF THE FIGURES

FIGS. 3A–J show the phenotypic conversion of THP-1 cells into macrophages upon stimulation by the indicated compounds.

FIGS. 4A–F shows cells treated with the indicated compounds to measure the ability of PPARγ agonists to prevent β-amyloid-stimulated conditioned media from THP-1 cells to induce a reactive astrocyte morphology. Cultures were fixed and stained for glial fibrillary acidic protein (GFAP).

FIGS. 15A–C shows the chemical structures of therapeutic compounds of the present invention.

FIG. 18 shows the sequence of the human 2.4 kb cox-2 gene promoter region (SEQ ID NO:1). The translation start site is at nucleotide 2328.

DEFINITIONS

Figure 1:
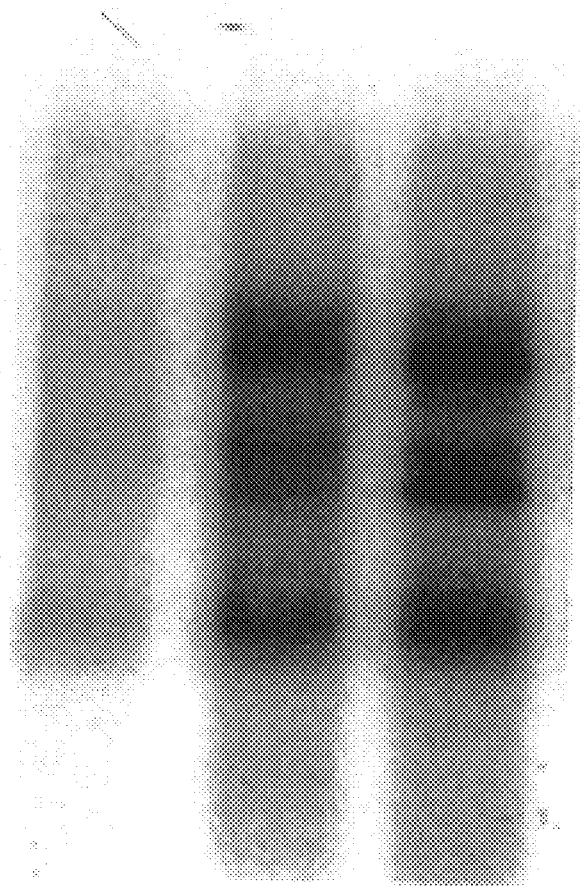
FIG. 1 shows an autoradiogram resolved by SDS-PAGE of tyrosine phosphorylated proteins in THP-1 cells stimulated by β-amyloid, monitored by immunoprecipitating tyrosine phosphorylated proteins using an anti-phosphotyrosine antibody.

To facilitate an understanding of the present invention, a number of terms and phrases are defined below:

As used herein, the term "therapeutically effective amount" refers to that amount of a composition that results in amelioration of symptoms or a prolongation of survival in a patient. A therapeutically relevant effect relieves to some extent one or more symptoms of a disease or condition or returns to normal either partially or completely one or more physiological or biochemical parameters associated with or causative of the disease or condition.

As used herein, the term "PPARγ agonist" refers to a compound or composition, which when combined with PPARγ, directly or indirectly stimulates or increases an in vivo or in vitro reaction typical for the receptor (e.g., transcriptional regulation activity). The increased reaction can be measured by any of a variety of assays known to those skilled in the art. A preferred PPARγ agonist is a thiazolidinedione compound, including, but not limited to, troglitazone, BRL 49653, pioglitazone, ciglitazone, WAY-120,744, englitazone, AD 5075, darglitazone, and congeners, analogs, derivatives, and pharmaceutically acceptable salts thereof.

As used herein, the term "regulatory element" refers to a deoxyribonucleotide sequence comprising the whole, or a portion of, an oligonucleotide sequence to which an activated transcriptional regulatory protein, or a complex comprising one or more activated transcriptional regulatory proteins, binds so as to transcriptionally modulate the expression of an associated gene or genes, including heterologous genes.

As used herein, the term "transcriptional regulatory protein" refers to cytoplasmic or nuclear proteins that, when activated, bind the regulatory elements/oligonucleotide sequences of the present invention either directly, or indirectly through a complex of transcriptional regulatory proteins or other adapter proteins, to transcriptionally modulate the activity of an associated gene or genes. Thus, transcriptional regulatory proteins can bind directly to the DNA regulatory elements of the present invention, or can bind indirectly to the regulatory elements by binding to another protein, which in turn binds to or is bound to a DNA regulatory element of the present invention.

As used herein, the term "transcriptionally modulate the expression of an associated gene or genes" means to change the rate of transcription of such gene or genes.

As used herein, the term "transplant" refers to tissue used in grafting, implanting, or transplanting, as well as the transfer of tissues from one part of the body to another, or the transfer of tissues from one individual to another, or the introduction of biocompatible materials into or onto the body. The term "transplantation" refers to the grafting of tissues from one part of the body to another part, or to another individual.

As used herein, the term "stem cell" or "undifferentiated cell" refers to self-renewing cells that are capable of giving rise to phenotypically and genotypically identical daughters as well as at least one other final cell type (e.g., terminally differentiated cells).

As used herein, the term "central nervous system" refers to all structures within the dura mater. Such structures include, but are not limited to, the brain and spinal cord.

As used herein, the terms "host" and "subject" refer to any animal, including, but not limited to, humans and non-human animals (e.g., rodents, arthropods, insects [e.g., Diptera], fish [e.g., zebrafish], non-human primates, ovines, bovines, ruminants, lagomorphs, porcines, caprines, equines, canines, felines, aves, etc.), which is to be the recipient of a particular treatment. Typically, the terms "host," "patient," and "subject" are used interchangeably herein in reference to a human subject. As used herein, the terms "subject suffering from Alzheimer's disease," "subject suffering from a disease with an inflammatory component," and "subject suffering from central nervous system injury," refer to subjects that are identified as having or likely having the particular disease, injury, or condition, respectively. As used herein the terms "subject susceptible to Alzheimer's disease" and "subject susceptible to a disease with an inflammatory component," refer to subjects identified as having a risk of contracting or developing the particular disease, injury, or condition, respectively. As used herein, the term "disease with an inflammatory component" refers to diseases and conditions that are associated with an inflammatory element. The inflammatory element can comprise a symptom, side-effect, or causative event associated with the disease or condition. Diseases with an inflammatory component include, but are not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDs dementia complex, and bacterial and viral meningitis.

As used herein, the term "neurological defect" refers to a defect involving or relating to the nervous system. Some neurological defects are caused by defective tissues or cells of the nervous system, while other defects are caused by defective tissues or cells that affect the nervous system. As used herein, the term "neurologically defective mammal" refers to a mammal having one or more neurological defects. When a neurological defect is "ameliorated," the condition of the host is improved. For example, amelioration can occur when defective tissue is returned partially or entirely to a normal state. However, amelioration can also occur when tissue remains subnormal, but is otherwise altered to benefit the host.

As used herein, the term "lesion" refers to a wound or injury, or to a pathologic change in a tissue.

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

The term "biologically active," as used herein, refers to a protein or other biologically active molecules (e.g., catalytic RNA) having structural, regulatory, or biochemical functions of a naturally occurring molecule.

The term "agonist," as used herein, refers to a molecule which, when interacting with an biologically active molecule, causes a change (e.g., enhancement) in the biologically active molecule, which modulates the activity of the biologically active molecule. Agonists include, but are not limited to proteins, nucleic acids, carbohydrates, lipids or any other molecules which bind or interact with biologically active molecules. For example, agonists can alter the activity of gene transcription by interacting with RNA polymerase directly or through a transcription factor or signal transduction pathway.

The terms "antagonist" or "inhibitor," as used herein, refer to a molecule which, when interacting with a biologically active molecule, blocks or modulates the biological activity of the biologically active molecule. Antagonists and inhibitors include, but are not limited to, proteins, nucleic acids, carbohydrates, lipids or any other molecules that bind or interact with biologically active molecules. Inhibitors and antagonists can effect the biology of entire cells, organs, or organisms (e.g., an inhibitor that slows or prevents neuronal degeneration and death).

The term "modulate," as used herein, refers to a change in the biological activity of a biologically active molecule. Modulation can be an increase or a decrease in activity, a change in binding characteristics, or any other change in the biological, functional, or immunological properties of biologically active molecules.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences which direct the termination of transcription, post-transcriptional cleavage and polyadenylation.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "oligonucleotide," refers to a short length of single-stranded polynucleotide chain. Oligonucleotides are typically less than 100 residues long (e.g., between 15 and 50), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review see, S. D. Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (R. Dijkema et al., EMBO J. 4:761 [1985]). Two other examples of promoter/enhancer elements active in a broad range of mammalian cell types are those from the human elongation factor 1α gene (T. Uetsuki et al, J. Biol. Chem., 264:5791 [1989]; D. W. Kim et al., Gene 91:217 [1990]; and S. Mizushima and S. Nagata, Nuc. Acids. Res., 18:5322 [1990]) and the long terminal repeats of the Rous sarcoma virus (C. M. Gorman et al., Proc. Natl. Acad. Sci. USA 79:6777 [1982]) and the human cytomegalovirus (M. Boshart et al, Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., *Molecular Cloning: A Laboratory Manual,* 2nd ed., Cold Spring Harbor Laboratory Press, New York [1989], pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHl/BclI restriction fragment and directs both termination and polyadenylation (J. Sambrook, supra, at 16.6–16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

The term "homology" refers to a degree of complementarity. There may be partial homology or complete homology (ie., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition below for "stringency").

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G}+\text{C})$, when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (D. L. Kacian et al., Proc. Natl. Acad. Sci. USA 69:3038 [1972]). Other nucleic acid will not be replicated by this amplification enzyme. Similarly, in the case of T7 RNA polymerase, this amplification enzyme has a stringent specificity for its own promoters (M. Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the tern "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "antisense" is used in reference to DNA or RNA sequences that are complementary to a specific DNA or RNA sequence (e.g, mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and antisense strands (i.e., the oligonucleotide or polynucleotide may be double-stranded).

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

Embryonal cells at various developmental stages can be used to introduce transgenes for the production of transgenic animals. Different methods are used depending on the stage of development of the embryonal cell. The zygote is a preferred target for micro-injection. In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438–4442 [1985]). As a consequence, all cells of the transgenic non-human animal will carry the incorporated transgene. This will, in general, also be reflected in the efficient transmission of the transgene to offspring of the founder since 50% of the germ cells will harbor the transgene. Micro-injection of zygotes is the preferred method for incorporating transgenes in practicing the invention. U.S. Pat. No. 4,873,191 describes a method for the micro-injection of zygotes; the disclosure of this patent is incorporated herein in its entirety.

Retroviral infection can also be used to introduce transgenes into an animal. The developing embryo can be cultured in vitro to the blastocyst stage. During this time, the blastomeres can be targets for retroviral infection (Janenich, Proc. Natl. Acad. Sci. USA 73:1260–1264 [1976]). Efficient infection of the blastomeres is obtained by enzymatic treatment to remove the zona pellucida (Hogan et al., in *Manipulating the Mouse Embryo,* Cold Spring Harbor Laboratory Press, Cold Spring Harbor, N.Y. [1986]). The viral vector system used to introduce the transgene is typically a replication-defective retrovirus carrying the transgene (D. Jahner et al., Proc. Natl. Acad Sci. USA 82:6927–693 [1985]). Transfection is easily and efficiently obtained by culturing the blastomeres on a monolayer of virus-producing cells (Van der Putten, supra; Stewart, et al, EMBO J. 6:383–388 [1987]). Alternatively, infection can be performed at a later stage. Virus or virus-producing cells can be injected into the blastocoele (D. Jahner et al, Nature 298:623–628 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

A third type of target cell for transgene introduction is the embryonal stem (ES) cell. ES cells are obtained by culturing pre-implantation embryos in vitro under appropriate conditions (Evans et al., Nature 292:154–156 [1981]; Bradley et al., Nature 309:255–258 [1984]; Gossler et al, Proc. Acad.

Sci. USA 83:9065–9069 [1986]; and Robertson et al., Nature 322:445–448 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468–1474 [1988]). Prior to the introduction of transfected ES cells into the blastocoel, the transfected ES cells may be subjected to various selection protocols to enrich for ES cells that have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell which has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk$^-$ cell lines, the CAD gene which is used in conjunction with CAD-deficient cells and the mammalian hypoxanthine-guanine phosphoribosyl transferase (hprt) gene which is used in conjunction with hprt$^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp.16.9–16.15.

As used herein, the term "purified" or "to purify" refers to the removal of contaminants from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labelled "A" and the antibody will reduce the amount of labelled A bound to the antibody.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that are used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

As used herein, the term "sample" is used in its broadest sense. In one sense it can refer to drugs and therapeutic compounds. In another sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. These examples are not to be construed as limiting the sample types applicable to the present invention.

General Description of the Invention

The present invention relates to methods and compositions for treating Alzheimer's disease and other diseases and conditions with an inflammatory component (e.g., central nervous system injury). In particular, the present invention provides agents that regulate the production of proinflammatory and neurotoxic products involved in Alzheimer's disease and other diseases and conditions with an inflammatory component including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDs dementia complex, and bacterial and viral meningitis.

The present invention further provides compositions and methods for drug screening and for identifying and characterizing factors that play a role in the cellular and molecular mechanisms involved in inflammatory responses. In particular, the present invention provides methods and compositions for identifying and characterizing factors that are involved in the regulation of cyclooxygenase-2 and signalling pathways regulating or regulated by cyclooxygenase-2.

Many aspects of the present invention are illustrated herein using Alzheimer's disease as a model. One of skill in the art will appreciate the general applicability of these examples to the treatment and regulation of a wide array of diseases and conditions with inflammatory components.

As discussed above, the therapeutic treatment strategies that have been used against Alzheimer's disease have targeted neurotransmitter replacement, or the preservation of normal brain structures, which potentially provide short-time relief, but do not prevent neuronal degeneration and death. In response to this need for more effective treatments against Alzheimer's disease, the present invention provides means to prevent neuronal degeneration and death through regulation of inflammatory processes.

The presence of inflammatory cytokines at elevated levels in the AD brain and the presence of a number of acute phase products has been reported. However, prior to the present invention, the molecular mechanisms underlying these inflammatory processes have not been sufficiently characterized, and safe, preventative therapies have not been developed to prevent the associated neuronal degeneration and death.

The principle pathological feature of AD is extracellular deposition of fibrillar amyloid and its compaction into senile plaques. The senile plaque is the focus of complex cellular reaction involving the activation of both microglia and astrocytes adjacent to the amyloid plaque. Microglia are the most abundant and prominent cellular component of the plaque. The plaque-associated microglia exhibit a "reactive" or "activated" phenotype and possess a ramified morphology whose processes envelop and invest the plaque. Microglia are the principal immune cell in the brain, are derived from a monocytic lineage, and are morphologically and functionally indistinguishable from macrophages. Like macrophages, microglia respond to various stimuli by acquisition of a "reactive" phenotype as evidenced by the elevated expression of a number of cell surface molecules, including MHC class II antigens, CD45, complement receptors CR3 and CR4, immunoglobulin receptors Fc$\gamma$RI and Fc$\gamma$RII, and ICAM-1. Activated microglia, like activated macrophages, secrete a diverse range of acute phase proteins including $\alpha$-antichymotrypsin, $\alpha$-antitrypsin, serum amyloid P, C-reactive protein, and complement components, among others (McGeer and Rogers, Neurology 42:447 [1992]). Importantly, activation of microglia results in the synthesis and secretion of the proinflammatory cytokines IL-1$\beta$, IL-6, and TNF-$\alpha$ and macrophage chemotactic protein-1.

In the AD brain, the association of microglia with the senile plaques is the most prominent and consistent cellular reaction to amyloid deposition (Cotman et al., Neurobiol. Aging 17:723 [1996]; Itagaki et al., J. Neuroimmunol. 24:173 [1989]; and Miyazono et al., Am J. Path. 139:589 [1991]). Plaque-associated microglia exhibit a reactive phenotype and display a ramified morphology investing the plaques with their processes (Itagaki et al., supra; Fukmoto et al., Neurodegen 5:13 [1996]; Mann et al., Acta Neuropath. 90:472 [1995]; and Perlmutter et al., Neurosci. Lett. 119:32 [1990]). Significantly, in transgenic mice expressing mutant forms of APP, the amyloid precursor protein, amyloid plaque formation is also accompanied by a subsequent appearance of activated microglia within and adjacent to the plaque core (Borchelt et al., Neuron 19:939 [1997]; Sturchler-Pierrat et al, Proc. Natl. Acad. Sci. 94:13287 [1997], Frautschy et al., Am. J. Pathol. 152:307 [1998]; and Masliah et al., J. Neurosci. 16:5795 [1996]). Furthermore, in animal models in which Aβ is directly injected into the brain, Aβ alone is sufficient to provoke recruitment of microglia to the amyloid deposits and mediates their activation (Weldon et al., J. Neurosci. 18:2161 [1998]). Thus, in both humans and mice, the presence of abundant and reactive microglia is an invariant response to amyloid deposition in the brain.

The compositions and methods of the present invention provide means to inhibit a diverse range of microglial response to Aβ. For example, the present invention provides agents that suppress a broad range of inflammatory responses (e.g., a broad range of Aβ-induced inflammatory responses in monocytes and microglia). These agents (e.g., PPARγ agonists) are shown to interact with the transcription factor PPARγ. The present invention also demonstrates that PPARγ agonists block the expression of cyclooxygenase-2 (COX-2) and the cytokines TNF-α and IL-6, and inhibit the secretion of neurotoxic products. Prior to the present invention, the therapeutic effects of PPARγ and PPARγ effectors in inflammatory disease were unexplored. Thus, the present invention provides novel therapeutic means for treating Alzheimer's disease and other diseases and conditions with an inflammatory component.

Detailed Description of the Invention

The present invention comprises methods and compositions for treating Alzheimer's disease and other diseases and conditions with an inflammatory component (e.g., central nervous system injury). In particular, the present invention provides agents that regulate the production of proinflammatory and neurotoxic products involved in Alzheimer's disease and other inflammatory diseases. The therapeutic agents of the present invention comprise PPARγ ligands (e.g., PPARγ agonists). Although it is not necessary to understand the mechanisms in order to practice the present invention, and it is not intended that the present invention be so limited, it is contemplated that the therapeutic agents of the present invention regulate the production of proinflammatory and neurotoxic through the alteration PPARγ activity and subsequent regulation of gene expression by PPARγ.

The PPARs are lipid-activated DNA binding proteins that are structurally related to the steroid and retinoic acid receptor families (Lemberger et al., Annu. Rev. Cell Dev. Biol. 12:335 [1996]). The activated form of the receptor binds to sequence-specific promoter elements, termed PPREs, and transcriptionally regulate gene expression (Ricote et al., Nature 391:79 [1998]). There are three PPAR isoforms (PPAR α, γ, and δ) which are differentially expressed. The natural ligands for this receptor family are fatty acids and lipid metabolites, with each PPAR family member displaying a distinct pattern of ligand specificity.

I. Therapeutic Agents of the Present Invention

The present invention demonstrates that agents that regulate PPARγ (e.g., PPARγ agonists) provide therapeutic compositions that regulate the production of proinflammatory and neurotoxic products involved in Alzheimer's disease and other inflammatory diseases (e.g., central nervous system injury). Such agents include, but are not limited to, prostaglandin $J_2$ (PGJ$_2$) and analogs thereof (e.g., $\Delta^{12}$-prostaglandin $J_2$ and 15-deoxy-$\Delta^{12,14}$-prostaglandin $J_2$), members of the prostaglandin $D_2$ family of compounds, docosahexaenoic acid (DHA), and thiazolidinediones (e.g., ciglitazone, troglitazone, pioglitazone, and BRL 49653). It is significant that most of the PPARγ agonists exhibit substantial bioavailability following oral administration and have little or no toxicity associated with their use (See e.g., Saltiel and Olefsky, Diabetes 45:1661 [1996]; Wang et al, Br. J. Pharmacol. 122:1405 [1997]; and Oakes et al, Metabolism 46:935 [1997]). The present invention contemplates that any known or future identified PPARγ agonist will find use with the present invention.

Compounds useful for practicing the present invention, and methods of making these compounds are disclosed in WO 91/07107; WO 92/02520; WO 94/01433; WO 89/08651; WO 96/33724; U.S. Pat. Nos. 4,287,200; 4,340, 605; 4,438,141; 4,444,779; 4,461,902; 4,572,912; 4,687, 777; 4,703,052; 4,725,610; 4,873,255; 4,897,393; 4,897, 405; 4,918,091; 4,948,900; 5,002,953; 5,061,717; 5,120, 754; 5,132,317; 5,194,443; 5,223,522; 5,232,925; 5,260, 445; and 5,814,647. The disclosure of these publications are incorporated herein by reference in their entireties.

As agents having the aforementioned effects the compounds of the following formulas are useful in treating individuals. Accordingly, in some embodiments of the present invention, the therapeutic agents comprise compounds of Formula I in FIG. 15, wherein $R_1$ and $R_2$ are the same or different, and each represents a hydrogen atom or a $C_1$–$C_5$ alkyl group; $R_3$ represents a hydrogen atom, a $C_1$–$C_6$ aliphatic acyl group, an alicyclic acyl group, an aromatic acyl group, a heterocyclic acyl group, an araliphatic acyl group, a ($C_1$–$C_6$ alkoxy)carbonyl group, or an aralkyloxycarbonyl group; $R_4$ and $R_5$ are the same or different, and each represents a hydrogen atom, a $C_1$–$C_5$ alkyl group or a $C_1$–$C_5$ alkoxy group, or $R_4$ and $R_5$ together represent a $C_1$–$C_5$ alkylenedioxy group; n is 1, 2, or 3; W represents the —CH$_2$—, >CO, or CH—OR$_6$ group (in which R$_6$ represents any one of the atoms or groups defined for $R_3$ and may be the same as or different, from $R_3$); and Y and Z are the same or different and each represents an oxygen atom or an imino (=NH) group; and pharmaceutically acceptable salts thereof.

Figure 15A:
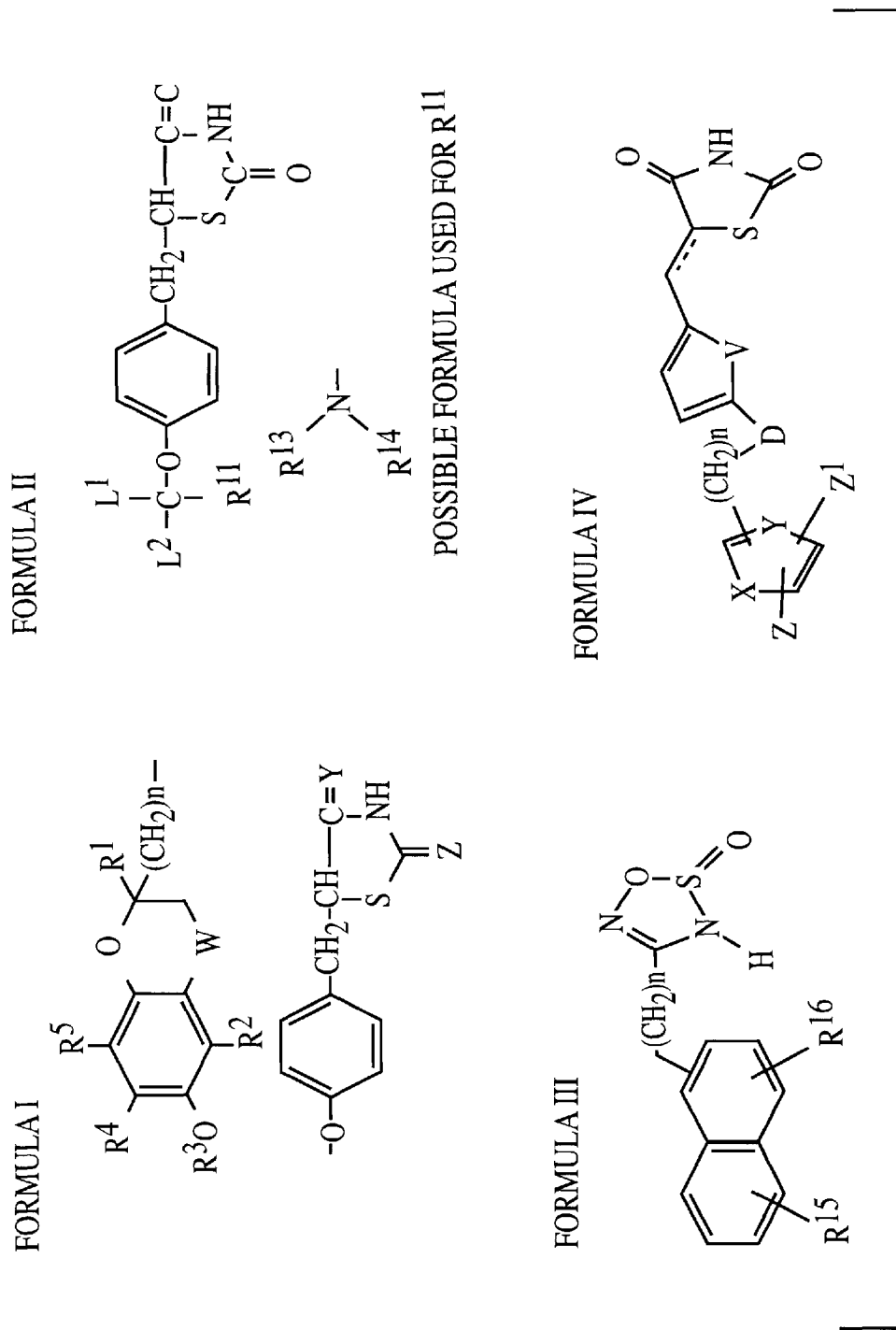
Figure 15B:
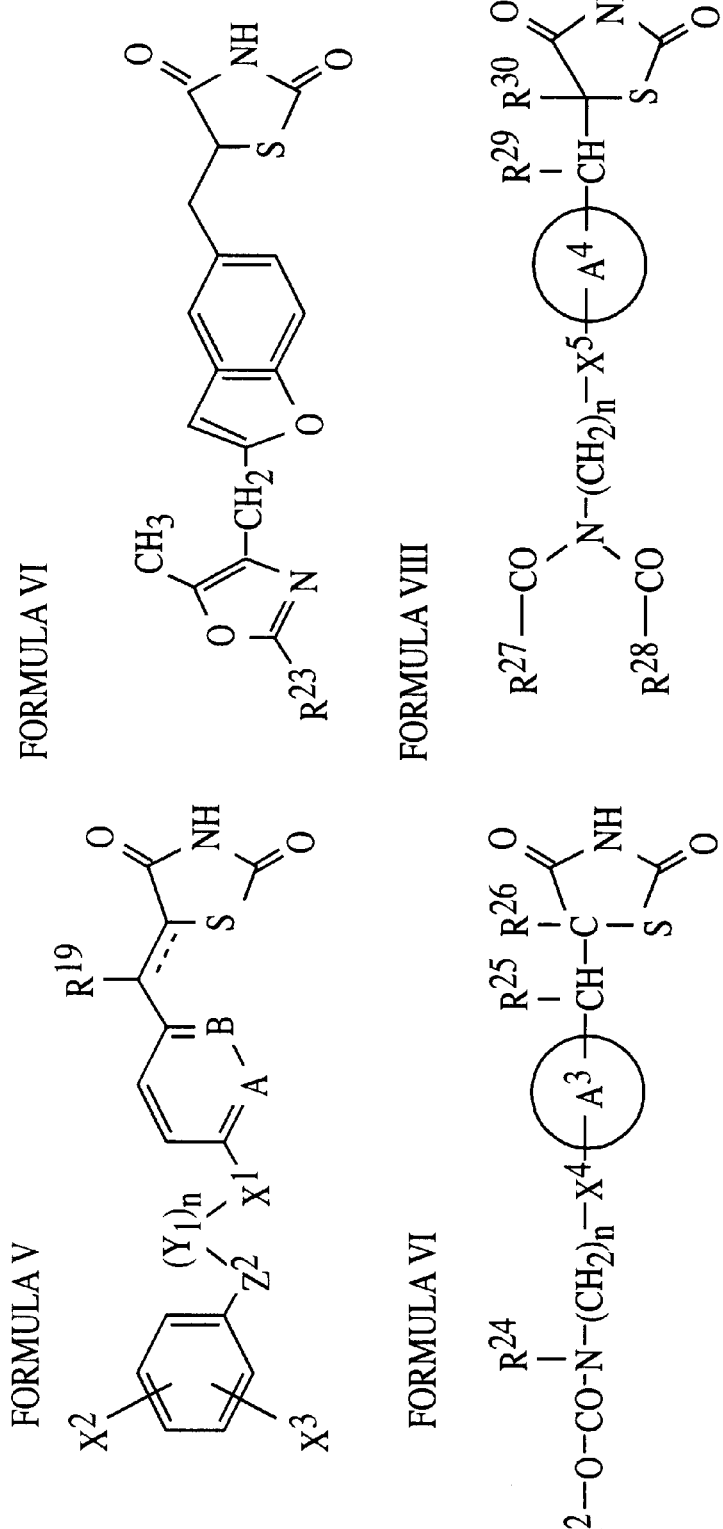

In some embodiments of the present invention, the therapeutic agents comprise compounds of Formula II in FIG. 15, wherein $R_{11}$ is a substituted or unsubstituted alkyl, alkoxy, cycloalkyl, phenylalkyl, phenyl, aromatic acyl group, a 5- or 6-membered heterocyclic group including 1 or 2 heteroatoms selected from the group consisting of nitrogen, oxygen, and sulfur, or a group of the formula indicated in FIG. 15 (i.e., the group labeled "Possible Formula Used for $R_{11}$") wherein $R_{13}$ and $R_{14}$ are the same or different and each is lower alkyl (alternately, $R_{13}$ and $R_{14}$ are combined to each other either directly or as interrupted by a heteroatom comprising nitrogen, oxygen, and sulfur to form a 5- or 6-membered ring); and wherein $L^1$ and $L^2$ are the same or different and each is hydrogen or lower alkyl or $L^1$ and $L^2$ are combined to form an alkylene group; or a pharmaceutically acceptable salt thereof.

In some embodiments of the present invention, the therapeutic agents comprise compounds of Formula III in FIG. 15, wherein $R_{15}$ and $R_{16}$ are independently hydrogen, lower alkyl containing 1 to 6 carbon atoms, alkoxy containing 1 to 6 carbon atoms, halogen, ethynyl, nitrile, methylthio, trifluoromethyl, vinyl, nitro, or halogen substituted benzyloxy; n is 0 to 4; or a pharmaceutically acceptable salt thereof.

In some embodiments of the present invention, the therapeutic agents comprise compounds of Formula IV in FIG. 15, wherein the dotted line represents a bond or no bond; V is—H=CH—, —N=CH—, —CH=N—, or S; D is $CH_2$, CHOH, CO, C=$NOR_{17}$, or CH=CH; X is S, O, $NR_{18}$, —CH=N, or —N=CH; Y is CH or N; Z is hydrogen, $(C_1-C_7)$alkyl, $(C_1-C_7)$cycloalkyl, phenyl, naphthyl, pyridyl, furyl, thienyl, or phenyl mono- or di-substituted with the same or different groups which are $(C_1-C_3)$alkyl, trifluoromethyl, $(C_1-C_3)$alkoxy, fluoro, chloro, or bromo; $Z^1$ is hydrogen or $(C_1-C_3)$alkyl; $R_{17}$ and $R_{18}$ are each independently hydrogen or methyl; and n is 1, 2, or 3; the pharmaceutically acceptable cationic salts thereof; and the pharmaceutically acceptable acid addition salts thereof when the compound contains a basic nitrogen.

In some embodiments of the present invention, the therapeutic agents comprise compounds of Formula V in FIG. 15, wherein the dotted line represents a bond or no bond; A and B are each independently CH or N, with the proviso that when A or B is N, the other is CH; $X^1$ is S, SO, $SO_2$, $CH_2$, CHOH, or CO; n is 0 or 1; $Y_1$ is $CHR^{20}$ or $R^{21}$, with the proviso that when n is 1 and $Y_1$ is $NR^{21}$, $X^1$ is $SO_2$ or CO; $Z^2$ is $CHR^{22}$, $CH_2CH_2$, cyclic $C_2H_2O$, CH=CH, $OCH_2$, $SCH_2$, $SOCH_2$, or $SO_2CH_2$; $R^{19}$, $R^{20}$, $R^{21}$, and $R^{22}$ are each independently hydrogen or methyl; and $X^2$ and $X^3$ are each independently hydrogen, methyl, trifluorormethyl, phenyl, benzyl, hydroxy, methoxy, phenoxy, benzyloxy, bromo, chloro, or fluoro; a pharmaceutically acceptable cationic salt thereof; or a pharmaceutically acceptable acid addition salt thereof when A or B is N.

In some embodiments of the present invention, the therapeutic agents comprise compounds of Formula VI in FIG. 15, or a pharmaceutically acceptable salt thereof, wherein $R^{23}$ is alkyl of 1 to 6 carbon atoms, cycloalkyl of 3 to 7 carbon atoms, phenyl or mono- or di-substituted phenyl wherein said substituents are independently alkyl of 1 to 6 carbon atoms, alkoxy of 1 to 3 carbon atoms, halogen, or trifluoromethyl.

In some embodiments of the present invention, the therapeutic agents comprise compounds of Formula VII in FIG. 15, or a tautomeric form thereof and/or a pharmaceutically acceptable salt thereof, and/or a pharmaceutically acceptable solvate thereof, wherein: $A^2$ represents an alkyl group, a substituted or unsubstituted aryl group, or an aralkyl group wherein the alkylene or the aryl moiety may be substituted or unsubstituted; $A^3$ represents a benzene ring having in total up to 3 optional substituents; $R^{24}$ represents a hydrogen atom, an alkyl group, an acyl group, an aralkyl group wherein the alkyl or the aryl moiety may be substituted or unsubstituted, or a substituted or unsubstituted aryl group; or $A^2$ together with $R^{24}$ represents substituted or unsubstituted $C_{2-3}$ polymethylene group, optional substituents for the polymethylene group being selected from alkyl or aryl or adjacent substituents together with the methylene carbon atoms to which they are attached form a substituted or unsubstituted phenylene group; $R^{25}$ and $R^{26}$ each represent hydrogen, or $R^{25}$ and $R^{26}$ together represent a bond; $X^4$ represents O or S; and n represents an integer in the range from 2 to 6.

In some embodiments of the present invention, the therapeutic agents comprise compounds of Formula VIII in FIG. 15, or a tautomeric form thereof and/or a pharmaceutically acceptable salt thereof, and/or a pharmaceutically acceptable solvate thereof, wherein: $R^{27}$ and $R^{28}$ each independently represent an alkyl group, a substituted or unsubstituted aryl group, or an aralkyl group being substituted or unsubstituted in the aryl or alkyl moiety; or $R^{27}$ together with $R^{28}$ represents a linking group, the linking group consisting or an optionally substituted methylene group or an O or S atom, optional substituents for the methylene groups including alky-, aryl, or aralkyl, or substituents of adjacent methylene groups together with the carbon atoms to which they are attached form a substituted or unsubstituted phenylene group; $R^{29}$ and $R^{30}$ each represent hydrogen, or $R^{29}$ and $R^{30}$ together represent a bond; $A^4$ represents a benzene ring having in total up to 3 optional substituents; $X^5$ represents O or S; and n represents an integer in the range of 2 to 6.

In some embodiments of the present invention, the therapeutic agents comprise compounds of Formula IX in FIG. 15, or a tautomeric form thereof and/or a pharmaceutically acceptable salt thereof, and/or a pharmaceutically acceptable solvate thereof, wherein: $A^5$ represents a substituted or unsubstituted aromatic heterocyclyl group; $A^6$ represents a benzene ring having in total up to 5 substituents; $X^6$ represents O, S, or $NR^{32}$ wherein $R^{32}$ represents a hydrogen atom, an alkyl group, an acyl group, an aralkyl group, wherein the aryl moiety may be substituted or unsubstituted, or a substituted or unsubstituted aryl group; $Y^2$ represents O or S; $R^{31}$ represents an alkyl, aralkyl, or aryl group; and n represents an integer in the range from 2 to 6. Suitable aromatic heterocyclyl groups include substituted or unsubstituted, single or fused ring aromatic heterocyclyl groups comprising up to 4 hetero atoms in each ring selected from oxygen, sulfur, or nitrogen. Favored aromatic heterocyclyl groups include substituted or unsubstituted single ring aromatic heterocyclyl groups having 4 to 7 ring atoms, preferably 5 or 6 ring atoms. In particular, the aromatic heterocyclyl group comprises 1, 2, or 3 heteroatoms, especially 1 or 2, selected from oxygen, sulfur, or nitrogen. Suitable values for $A^5$ when it represents a 5-membered aromatic heterocyclyl group include thiazolyl and oxazoyl, especially oxazoyl. Suitable values for $A^6$ when it represents a 6-membered aromatic heterocyclyl group include pyridyl or pyrimidinyl. Suitable $R^{31}$ represents an alkyl group, in particular a $C_{1-6}$ alkyl group (e.g., a methyl group). Preferably, $A^5$ represents a moiety of formula (a), (b), or (c), in FIG. 15, under Formula IX: formula (a), (b), and (c) wherein: $R^{33}$ and $R^{34}$ each independently represents a hydrogen atom, an alkyl group, or a substituted or unsubstituted aryl group or when $R^{33}$ and $R^{34}$ are each attached to adjacent carbon atoms, then $R^{33}$ and $R^{34}$ together with the carbon atoms to which they are attached form a benzene ring wherein each carbon atom represented by $R^{33}$ and $R^{34}$ together may be substituted or unsubstituted; and in the moiety of Formula (a), $X^7$ represents oxygen or sulphur. In one preferred embodiment of the present invention, $R^{33}$ and $R^{34}$ together present a moiety of Formula (d) in FIG. 15, under Formula IX: wherein $R^{35}$ and $R^{36}$ each independently represent hydrogen, halogen, substituted or unsubstituted alkyl, or alkoxy.

In some embodiments of the present invention, the therapeutic agents comprise compounds of Formula X in FIG. 15, or a tautomeric form thereof and/or a pharmaceutically acceptable salt thereof, and/or a pharmaceutically acceptable solvate thereof, wherein: $A^7$ represents a substituted or unsubstituted aryl group; $A^8$ represents a benzene ring having in total up to 5 substituents; $X^8$ represents O, S, or $NR^9$, wherein $R^{39}$ represents a hydrogen atom, an alkyl group, an acyl group, an aralkyl group, wherein the aryl moiety may be substituted or unsubstituted, or a substituted or unsubstituted aryl group; $Y^3$ represents O or S; $R^{37}$ represents hydrogen; $R^{38}$ represents hydrogen or an alkyl, aralkyl, or aryl group or $R^{37}$ together with $R^{38}$ represents a bond; and n represents an integer in the range from 2 to 6.

In some embodiments of the present invention, the therapeutic agents comprise compounds of Formula XI in FIG. 15, or a tautomeric form thereof and/or a pharmaceutically acceptable salt thereof, and/or a pharmaceutically acceptable solvate thereof, wherein: $A^1$ represents a substituted or unsubstituted aromatic heterocyclyl group; $R^1$ represents a hydrogen atom, an alkyl group, an acyl group, an aralkyl group, wherein the aryl moiety may be substituted or unsubstituted, or a substituted or unsubstituted aryl group; $A^2$ represents a benzene ring having in total up to 5 substituents; and n represents an integer in the range of from 2 to 6. Suitable aromatic heterocyclyl groups include substituted or unsubstituted, single or fused ring aromatic heterocyclyl groups comprising up to 4 hetero atoms in each ring selected from oxygen, sulfur, or nitrogen. Favored aromatic heterocyclyl groups include substituted or unsubstituted single ring aromatic heterocyclyl groups having 4 to 7 ring atoms, preferably 5 or 6 ring atoms. In particular, the aromatic heterocyclyl group comprises 1, 2, or 3 heteroatoms, especially 1 or 2, selected from oxygen, sulfur, or nitrogen. Suitable values for $A^1$ when it represents a 5-membered aromatic heterocyclyl group include thiazolyl and oxazolyl, especially oxazoyl. Suitable values for $A^1$ when it represents a 6-membered aromatic heterocyclyl group include pyridyl or pyrimidinyl.

In some embodiments of the present invention, the therapeutic agents comprise compounds of Formulas XII and XIII in FIG. 15, or pharmaceutically acceptable salts thereof wherein the dotted line represents a bond or no bond; R is cycloalkyl of three to seven carbon atoms, naphthyl, thienyl, furyl, phenyl, or substituted phenyl wherein the substituent is alkyl of one to three carbon atoms, alkoxy of one to three carbon atoms, trifluoromethyl, chloro, fluoro, or bis (trifluoromethyl); $R^1$ is alkyl of one to three carbon atoms; X is O or C=O; A is O or S; and B is N or CH.

Some embodiments of the present invention include the use of the compounds of Formulas I through XIII for the treatment of Alzheimer's disease as well as diseases and conditions with inflammatory components. These compounds are herein referred to as thiazolidine derivatives. Where appropriate, the specific names of thiazolidine derivatives may be used including: troglitazone, ciglitazone, pioglitazone, and BRL 49653.

A preferred group of compounds are those of Formula XI, wherein the dotted line represents no bond, $R^1$ is methyl, X is O and A is O. Especially preferred within this group are the compounds where R is phenyl, 2-naphthyl and 3,5-bis (trifluoromethyl)phenyl. Another group of preferred compounds are those of Formula XIII, wherein the dotted line represents no bond, $R^1$ is methyl and A is O. Particularly preferred compounds within this group are compounds where B is CH and R is phenol, p-tolyl, m-tolyl, cyclohexyl, and 2-naphthyl. In alternative embodiments of the present invention, the B is N and R is phenyl.

In still further embodiments, the present invention provides methods for the use of a pharmaceutical composition suitable for administering an effective amount of at least one composition comprising Formulas I through XIII, in unit dosage form. In alternative embodiments, the composition further comprise a pharmaceutically acceptable carrier.

Specific examples of compounds of the present invention include, but are not limited to: (+)-5-[[4-[3,4-dihydro-6-hydroxy-2,5,7,8-tetramethyl-2H-1-benzopyran-2-yl) methoxy]phenyl]methyl]-2,4-thiazolidinedione (troglitazone); 4-(2-naphthylmethyl)-1,2,3,5-oxathiadiazole-2-oxide; 5-[4-[2-[N-(benzoxyazol-2-yl)-N-methylamino]ethoxy]benzyl]-5-methylthiazolidine-2,4-dione; 5-[4-[2-[2,4-dioxo-5-phenylthiazolidin-3-yl)ethoxy] benzyl]thiazolidine-2,4-dione; 5-[4-[2-[-N-methyl-N-(phenoxycarbonyl)amino]ethoxy]benzyl]thiazolidine-2,4-dione; 5-[4-(2-(phenoxyethoxy)benzyl]thiazolidine-2,4-dione; 5-[4-[2-(4-(chlorophenyl)ethylsulfonyl]benzyl] thiazolidine-2,4-dione; 5-[4-[3-(5-methyl-2-phenyloxazol-4-yl)propionyl]benzyl]thiazolidine-2,4-dione; 5-[4-[(1-methylcyclohexyl)methoxy]benzyl]thiadiazolidine-2,4-dione (ciglitazone); 5-[[4-(3-hydroxy-1-methylcyclohexyl) methoxy]benzyl]thiadiazolidine-2,4-dione; 5-[4-[2-(5-methyl-2-phenyloxazol-4-yl)ethoxyl]benzyl] thiadizolidine-2,4-dione; 5-[4-[2-(5-ethylpyridin-2-yl) ethoxyl]benzyl]thiadiazolidine-2,4-dione (pioglitazone); 5-[(2benzyl-2,3-dihydrobenzopyran)-5-ylmethyl] thiadiazoline-2,4-dione (englitazone); 5-[[2-(2-naphthylmethyl)benzoxazol]-5-ylmethyl]thiadiazoline-2,4,-dione; 5-[4-[2-(3-phenylureido)ethoxyl]benzyl] thiadiazoline-2,4-dione; 5-[4-[2-[N-(benzoxazol-2-yl)-N-methylamino]ethoxy]benzyl]thiadiazoline-2,4-dione; 5-[4-[3-(5-methyl-2-phenyloxazol-4-yl)propionyl]benzyl] thiadiazoline-2,4-dione; 5-[2-(5-methyl-2-phenyloxazol-4-ylmethyl)benzofuran-5-ylmethyl]-oxazolidine-2,4-dione;5-[4-[2-[N-methyl-N-(2-pyridyl)amino]ethoxy]benzyl] thiazolidine-2,4-dione (BRL49653); and 5-[4-[2-[N (benzoxazol-2-yl)-N-methylamino]ethoxy]benzyl]-oxazolidine-2,4-dione.

Figure 16:
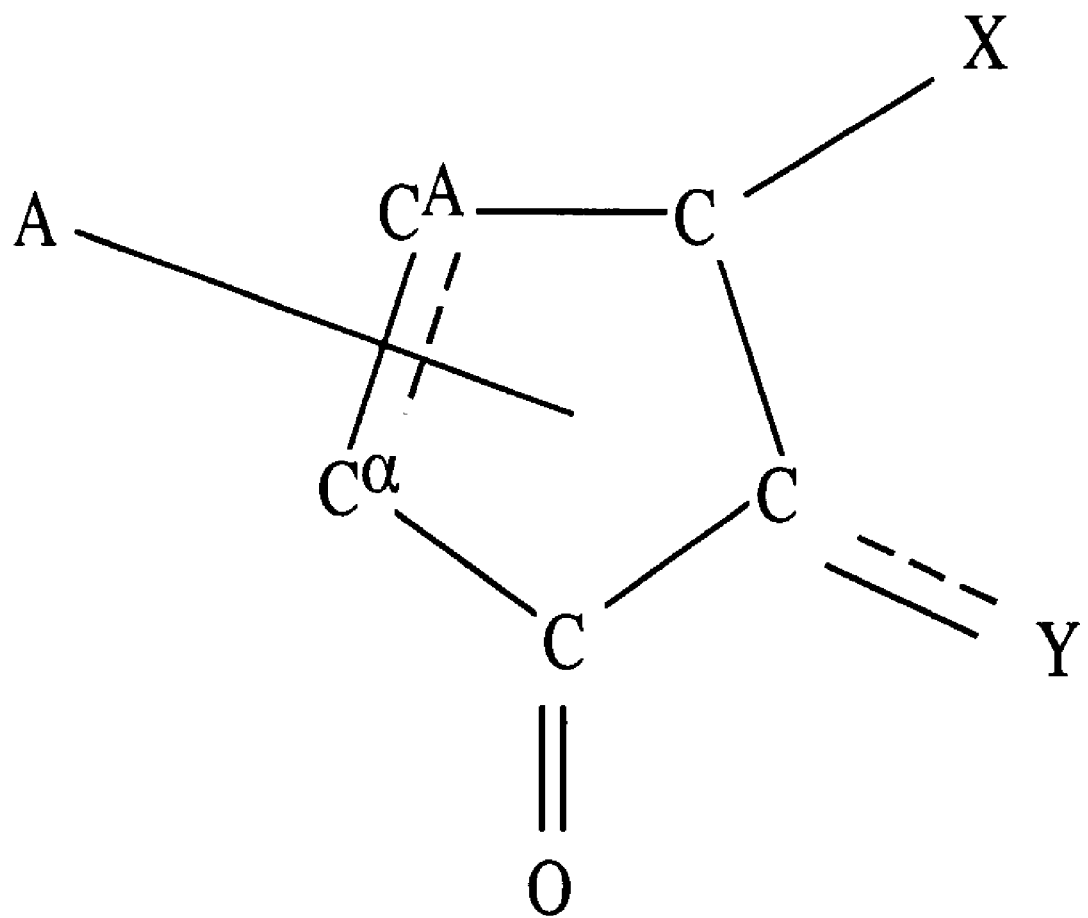
FIG. 16 shows the chemical structures of therapeutic compounds of the present invention.

In yet other embodiments of the present invention, the therapeutic agents comprise compounds having the structure shown in FIG. 16, wherein: A is selected from hydrogen or a leaving group at the α- or β- position of the ring, or A is absent when there is a double bond between the $C^\alpha$ and $C^\beta$ of the ring; X is an alkyl, substituted alkyl, alkenyl, substituted alkenyl, alkynyl, or substituted alkynyl group having in the range of 2 up to 15 carbon atoms; and Y is an alkyl, substituted alkyl, alkenyl, substituted alkenyl, alkynyl, or substituted alkynyl group having in the range of 2 up to 15 carbon atoms. As used herein, the term "leaving group" refers to functional groups which can readily be removed from the precursor compound, for example, by nucleophilic displacement, under $E_2$ elimination conditions, and the like. Examples include, but are limited to, hydroxy groups, alkoxy groups, tosylates, brosylates, halogens, and the like.

The therapeutic agents of the present invention (e.g., the compounds in Formulas I–XIII in FIG. 15) are capable of further forming both pharmaceutically acceptable acid addition and/or base salts. All of these forms are within the scope of the present invention.

Pharmaceutically acceptable acid addition salts of the present invention include, but are not limited to, salts derived from nontoxic inorganic acids such as hydrochloric, nitric, phospohoric, sulfuric, hydrobromic, hydriodic, hydrofluoric, phosphorous, and the like, as well as the salts derived form nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bissulfite, nitrate, phosphate, monohydrogenphosphate, dihydrogenphosphate, metaphosphate, pyrophosphate, chloride, bromide, iodide, acetate, trifluoracetate, propionate, caprylate, isobutyrate, oxalate, malonate, succinate, suberate, sebacate, fumarate, malcate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like, as well as gluconate, galacturonate, and n-methyl glucamine (See e.g., Berge et al., J. Pharm. Science 66:1 [1977]).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner or as described above. The free base forms differ from their respective salt forms somewhat in certain physical properties such as solubility in polar solvents, but are otherwise equivalent to their respective free base for purposes of the present invention.

Pharmaceutically acceptable base addition salts are formed with metals or amines, such as alkali and alkaline earth metals or organic amines. Examples of metals used as cations include, but are not limited to, sodium, potassium, magnesium, calcium, and the like. Examples of suitable amines include, but are not limited to, $N_2N'$-dibenzylethylenediamine, chloroprocaine, choline, diethanolamine, dicyclohexylamine, ethylenediamine, N-methylglucamine, and procaine (See e.g., Berge et al., J. Pharm. Science 66:1 [1977]).

The base addition salts of the acidic compounds are prepared by contacting the free acid form with a sufficient amount of the desired base to produce the salt in the conventional manner. The free acid form may be regenerated by contacting the salt form with an acid and isolating the free acid in the conventional manner or as described above. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including, but not limited to, hydrated forms. In general, the solvated forms, including hydrated forms, are equivalent to unsolvated forms and are intended to be encompassed within the scope of the present invention. Certain of the compounds of the present invention possess one or more chiral centers and each center may exist in different configurations. The compounds can, therefore, form stereoisomers. Although these are all represented herein by a limited number of molecular formulas, the present invention includes the use of both the individual, isolated isomers and mixtures, including racemates, thereof. Where stereospecific synthesis techniques are employed or optically active compounds are employed as starting materials in the preparation of the compounds, individual isomers may be prepared directly. However, if a mixture of isomers is prepared, the individual isomers may be obtained by conventional resolution techniques, or the mixture may be used as is, with resolution.

Furthermore, the thiazolidene or oxazlidene part of the compounds of Formulas I through XIII can exist in the form of tautomeric isomers, and are intended to be a part of the present invention.

For preparing pharmaceutical compositions from the compounds of the present invention, pharmaceutically acceptable carriers can be in any suitable form (e.g., solids, liquids, gels, etc.). Solid form preparations include, but are not limited to, powders, tablets, pills, capsules, cachets, suppositories, and dispersible granules. A solid carrier can be one or more substances which may also act as diluents, flavoring agents, binders, preservatives, tablet disintegrating agents, or an encapsulating material. The present invention contemplates a variety of techniques for administration of the therapeutic compositions. Suitable routes include, but are not limited to, oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, among others. Indeed, it is not intended that the present invention be limited to any particular administration route.

For injections, the agents of the present invention may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

In powders, the carrier is a finely divided solid which is in a mixture with the finely dived active component. In tablets, the active component is mixed with the carrier having the necessary binding properties in suitable proportions, which has been shaped into the size and shape desired.

The powders and tablets preferably contain from five or ten to about seventy percent of the active compounds. Suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter and the like, among other embodiments (e.g., solid, gel, and liquid forms). The term "preparation" is intended to also encompass the formation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, in some embodiments of the present invention, a low melting wax, such as a mixture of fatty acid glycerides or cocoa butter, is first melted and the active compound is dispersed homogeneously therein, as by stirring. The molten homogenous mixture is then poured into convenient sized molds, allowed to cool, and thereby to solidify in a form suitable for administration.

Liquid form preparations include, but are not limited to, solutions, suspensions, and emulsions (e.g., water or water propylene glycol solutions). For parenteral injection, in some embodiments of the present invention, liquid preparations are formulated in solution in aqueous polyethylene glycol solution. Aqueous solutions suitable for oral use can be prepared by dissolving the active component in water and adding suitable colorants, flavors, and stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 100 mg, preferably ranging from 0.5 mg to 100 mg according to the particular application and the potency of the active component. The composition can, if desired, also contain other compatible therapeutic agents. General procedures for preparing pharmaceutical compositions are described in Remington's Pharmaceutical Sciences, E. W. Martin ed., Mack Publishing Co., PA (1990).

The assessment of the clinical features and the design of an appropriate therapeutic regimen for the individual patient is ultimately the responsibility of the prescribing physician. It is contemplated that, as part of their patient evaluations, the attending physicians know how to and when to terminate, interrupt, or adjust administration due to toxicity, or to organ dysfunctions. Conversely, the attending physicians also know to adjust treatment to higher levels, in circumstances where the clinical response is inadequate, while precluding toxicity. The magnitude of an administrated dose in the management of the disorder of interest will vary with the severity of the condition to be treated, the patient's individual physiology, biochemisty, etc., and to the route of administration. The severity of the condition, may, for example, be evaluated, in part, by standard prognostic evaluation methods. Further, the dose and dose frequency will also vary according to the age, body weight, sex and response of the individual patient.

II. Activity of the Therapeutic Agents

The therapeutic agents described above find use in the treatment of Alzheimer's disease, as well as diseases and conditions with inflammatory components, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDs dementia complex, and bacterial, parasitic, fungal, and viral meningitis and encephalitis. The following description provides examples illustrating the activity of the therapeutic agents.

During the development of the present invention, experiments demonstrated that PPARγ agonists blocked the Aβ-stimulation-induced macrophage differentiation (See e.g., Example 2). Additionally, PPARγ agonists blocked the microglial-mediated activation of astrocytes and prevented monocyte-mediated neurotoxicity (See e.g., Examples 3 and 4). One consequence of microglial activation by Aβ or other immune stimuli is the stimulation of cytokine production. The PPARγ agonists of the present invention were also shown to inhibit the expression of the cytokines interleukin-6 (IL-6) and TNF-α (See e.g., Example 5). The PPARγ agonists also inhibited the expression of COX-2 (See e.g., Example6). These observations demonstrated that the therapeutic agents of the present invention provide novel therapeutic approaches for the suppression of COX-2 action in Alzheimer's disease and other inflammatory disorders.

The COX-2 gene is an immediate early gene and its transcriptional activation is mediated through uncharacterized signaling pathways (Smith et al., J. Biol. Chem. 271:33157 [1996]). Lipopolysaccharide (LPS)-stimulated COX-2 induction has been investigated in microglia and macrophages and these studies have established that NF-κB is required for its expression (Bauer et al., Eur. J. Biochem. 243:726 [1997]; and Hwang et al., Biochem Pharmacol 54:87 [1997]), consistent with data from other cell lines (Inoue et al., J. Biol. Chem. 270:24965 [1995]; and Yamanoto et al., J. Biol. Chem. 270:31315 [1995]). Although the COX-2 promoter possesses a number of positive regulatory elements, including an essential cAMP response element (CRE), beyond a requirement for NF-κB, prior to the present invention it was unclear how COX-2 expression was regulated and what signaling pathways impinged on the promoter of this gene. Furthermore, the present invention provides the first negatively acting element identified in the COX-2 promoter.

Furthermore, experiments conducted during the development of the present invention demonstrated that Aβ treatment of monocytes and macrophages resulted in the rapid and sustained induction of COX-2 expression (See e.g., Examples 6 and 7). Importantly, these experiments demonstrated that the induction of COX-2 by phorbol ester was dramatically inhibited by PPARγ agonists due to their action on cis-acting promoter elements. The finding that COX-2 expression was inhibited by PPARγ agonists through their action on inhibitory promoter elements provides alternative therapeutic options for inhibition of synthesis of proinflammatory agents (e.g., prostaglandin $E_2$).

Experiments conducted during the development of the present invention also demonstrated that PPARγ agonists potently inhibited a diverse range of microglial responses to Aβ. Thus, these agents find use as therapeutic agents in the treatment of Alzheimer's disease and other disorders with a significant inflammatory component (e.g., stroke, traumatic injury, and spinal injury, among others). As discussed above, most of the PPARγ agonists exhibit substantial bioavailability following oral administration and have little or no toxicity associated with their use (See e.g., Saltiel and Olefsky, Diabetes 45:1661 [1996]; Wang et al., Br. J. Pharmacol. 122:1405 [1997]; and Oakes et al., Metabolism 46:935 [1997]). Thus, the present invention provides methods and compositions for attenuating the progressive neurodegenerative processes in Alzheimer's disease and other diseases and conditions with an inflammatory component. However, it is not intended that the present invention be limited to any particular mechanism. Indeed, an understanding of the mechanisms is not necessary in order to practice the present invention.

To further illustrate the general applicability of the methods and compositions of the present invention, experiments were conducted to demonstrate their ability to treat central nervous system injury, and in particular, to treat inflammation and prevent secondary damage following injury. It has long been recognized that injury to the mammalian central nervous system (CNS) leads to permanent disability. One of the most important and yet poorly understood consequences of CNS injury is the uniquely progressive nature of some injuries to the brain and spinal cord. This problem that has plagued the field of CNS injury research for many years is the progressive necrosis and development of cavities or cysts as secondary events following trauma to the CNS. Such cavitation can develop from a small initial lesion that progresses to a large cavity extending far rostral and caudal to the original area of injury (Balentine, Lab. Invest. 39:236 [1978]). While investigators have hypothesized that cavitation and central necrosis is related to ischemic injury (Balentine, supra), hemorrhage (Ducker et al., J. Neurosurg. 35:700 [1971]; and Wallace et al., Surg. Neurol. 27:209 [1987]), neuronal lysozyme activity (Kao et al., J. Neurosurg 46:757 [1977]), or leakage of serum proteins across the blood brain barrier (Fitch and Silver, Exp. Neuro. 148:587 [1997]), much evidence points to macrophage infiltration and inflammation as being key to this pathological process (Blight, Neuroscience 60:263 [1994]; Szczepanik et al., Neuroscience 70:57 [1996]; Fitch and Silver, supra; and Zhang et al., Exp. Neurology 143:141 [1997]). This is an important therapeutic target for further study, as an acellular cyst lacks the appropriate cellular substrates for axon regeneration to occur (Guth et al., Exp. Neurol. 88:1 [1985]). In addition, this inflammatory response also involves the local synthesis and secretion of cytokines, in particular TNF-α, IL-1β, and IL-6.

The inflammatory response that occurs in the central nervous system (CNS) following injury is composed primarily of two components: activation of intrinsic microglial cells and recruitment of bone marrow-derived macrophages and other inflammatory cells from the peripheral bloodstream. This response to injury is thought by many investigators to contribute to secondary damage within the CNS (See e.g., Blight, Neuroscience 60:263 [1994]). Microglial cytokines have also been suggested as possible sources of nervous system impairment following injury (Giulian et al., J. Neurosci. 9:4416 [1989]), and neutrophilic leukocytes may augment necrosis and inflammation following a CNS injury (Means and Anderson, J. Neuropathol. Exp. Neurol. 42:707 [1983]). Microglial cells are capable of releasing cytotoxic factors that can kill neurons (Banati et al., Glia 7:111 [1993]; and Giulian, Glia 7:102 [1993]), and have been suggested to play a role in disconnecting existing neuronal connections and destroying neurons surrounding areas of injury (Giulian et al., Neurochem. Int. 25:227 [1994]; and Giulian et al., Dev. Neurosci. 16:128 [1994]). Many authors have advocated the use of therapeutic agents to modify the secretory activity of microglia/macrophages as a way to limit secondary damage to the CNS (See e.g., Giulian and Lachman, Science 228:497 [1985]; Giulian et al.,[1989], supra; Banati et al., supra; Guth et al., Exp. Neurol. 126:76 [1994; Guth et al., Proc. Natl. Acad. Sci. 91:12308 [1994]; and Zhang et al., supra).

This secondary damage in the CNS following trauma often results in progressive necrosis and cystic cavitation and can lead to dramatic increases in the size and magnitude of an injury. Various anti-inflammatory agents have been tested in animal models to determine whether they can limit the spread of progressive necrosis (Zhang, et al., supra). Experiments conducted during the development of the present invention demonstrate that PPARγ agonists find use in the prevention of cystic cavitation and provide means to improve the clinical outcome following CNS injuries.

Experiments conducted during the development of the present invention used a tissue culture model for progressive necrosis to compare the reactions of astrocytes in confluent monolayers to the introduction of activated or non-activated macrophages, similar to the sequence of events following trauma in the nervous system (See e.g., Example 8). As found in vivo after injury, the model of the present invention allows direct contact and interaction between the two major cell types. The number of live and dead cells of each type were quantitatively measured and the size of the "culture cavities" was determined for each culture. These cavities were observed as areas of the culture that were devoid of cells (i.e., areas previously covered by the confluent monolayer of astrocytes that were subsequently devoid of cells). This is analogous to the astrocyte-free areas found in cystic cavities that result from progressive necrosis after an injury to the brain or spinal cord. These cavities can result from astrocyte death, astrocyte migration, or various combinations of both processes.

Figure 17:
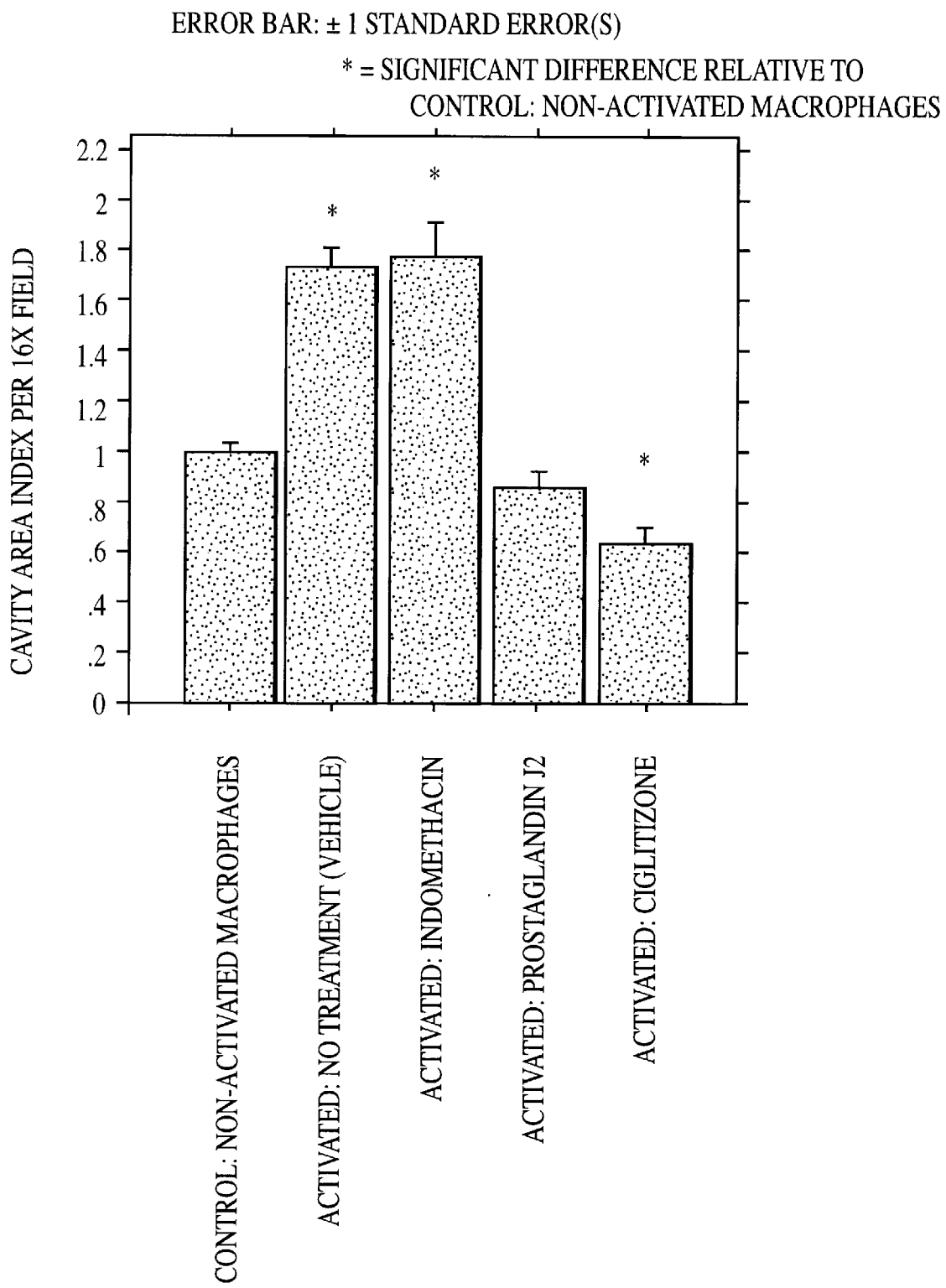
FIG. 17 shows a graph representing the effects of various PPARγ agonists on a cell culture model of central nervous system secondary injury.

The graph in FIG. 17 presents quantitative analysis of the changes in astrocyte-macrophage co-cultures by activation of macrophages and treatment with anti-inflammatory PPARγ agonists. Each treatment category is expressed relative to the appropriate drug or vehicle treated non-activated macrophage control, with the average for each control group being set to 1. Asterisks denote statistical significance ($p<0.05$) relative to the pooled "Control: Non-Activated Macrophage" category by Fisher's PLSD for ANOVA. As shown in FIG. 17, activated macrophages induced changes in the astrocyte culture that mimic the development of cavities found after CNS injury. The area of astrocyte withdrawal per microscopic field was significantly increased by activated macrophages with no treatment (vehicle), which is analogous to the cavitation found after an in vivo CNS injury. Indomethacin treatment (100 $\mu$M) of the activated macrophages did not prevent this increase in area of the culture cavity relative to control levels. In contrast, prostaglandin $J_2$ treatment (10 $\mu$M) and Ciglitazone treatment (50 $\mu$M) of the activated macrophages, while interacting with the astrocyte cultures, abolished the increases in area of culture cavities relative to their control levels with non-activated macrophages. In the case of Prostaglandin $J_2$, the average size of culture cavitation per field was maintained at control levels (i.e., the increase in cavity size was prevented), while Ciglitazone significantly decreased the size of the cavities per field below that of control.

These results qualitatively and quantitatively demonstrate that PPARγ agonists can effectively block the destructive effects of activated macrophages in progressive necrosis associated with CNS injury. These results also demonstrate that the methods and compositions (e.g., PPARγ agonists) of the present invention find important therapeutic use in the in vivo treatment of spinal cord and brain injuries to prevent the inflammatory sequelae that lead to secondary damage in increases in the severity of the initial trauma.

The following description provides test models for evaluating dosage and treatment conditions for several clinical indications of the present invention. These examples are provided to illustrate the array of indications and general procedures used in such therapies, and are not intended to limit the present invention to use with these specific examples. One skilled in the art will appreciate the broad applicability of these procedures to a wide variety of clinical indications. It is understood that variations may be made with respect to the models chosen and the implementation of the therapy without departing from the spirit of the present invention.

A. Multiple Sclerosis and Immune-Mediated Neuropathies

It is contemplated that treatment with the therapeutic agents of the present invention finds use in conjunction with animal disease models for multiple sclerosis and immune-mediated neuropathies. The principal animal model for multiple sclerosis (MS), Guillain-Barre syndrome, and allied autoimmune diseases is the rodent experimental autoimmune neuritis (EAN) (See e.g., Gaupp et al., J. Neuroimmunol. 79:129 [1997]; and Ho et al, Ann. Rev. Neurosci. 21:187 [1998]).

Thus, in some embodiments, the methods and compositions of the present invention find use in determining the efficacy of PPARγ agonists in suppressing the clinical and pathological markers. EAN provokes extensive demyelination, clinical neurological deficits and paralysis, apparently due to the activation of lymphocytes, macrophages and monocytes, and associated induction of cytokine expression. It is contemplated that proinflammatory cytokines are linked to the primary pathological features of the disease and inhibition of their expression will diminish the magnitude of the pathological effects and clinical outcome.

Trials are contemplated in which the Lewis rat model of EAE is used, as this strain of rats is susceptible to EAE, due to the presence of an autosomal dominant gene linked to the MHC gene cluster (Zhu et al., J. Neuroimmunol. 84:40 [1998]; and Martiney et al., J. Immunol. 160:5588 [1998]). In these trials, Lewis rats are immunized with peripheral nervous system myelin in Freund's complete adjuvant. The rats subsequently develop peripheral limb weakness, which ultimately progresses to paralysis. The neurological deficits are evaluated on a 0–5 scale, in which 0 indicates no observable deficits and 5 reflects complete paralysis. Time of onset and severity of clinical impairment are evaluated over a period of 45 days. Cytokine expression is evaluated throughout this interval using RT-PCR for a semi-quantitative analysis of TNF-$\alpha$, IL-1$\beta$, and IL-6 mRNA levels from both brain and spinal cord. The animals orally receive the PPAR$\gamma$ agonists, Troglitazone (Rezulin) (10–50 mg/kg), docosahexanoic acid (100 mg/kg) and indomethacin (2 mg/kg), or vehicle (control). A first set of trials is conducted whereby the animals are treated with the therapeutic agents starting at the time of immunization and continued throughout the 45 day evaluation period. After the initial trial, the dose of therapeutic agents is reevaluated and trials are performed in which the drug administration is delayed until the time of onset of symptoms.

B. Stroke and Ischemic Brain Injuries

Proinflammatory cytokines play a critical role in the progressive neuropathological changes that accompany stroke and other ischemic brain injuries (Sharma and Kumar, Metab. Brain Dis. 13:1 [1998]; and Rothwell et al., J. Clin. Invest. 100:2648 [1998]). Ischemia in the brain is followed by the induction of expression of a variety of cytokines (particularly IL-1$\beta$, TNF-$\alpha$, and IL-6), that have been mechanistically linked to neuropathological changes in the brain. Experimental interventions in which cytokine actions are inhibited have been reported to ameliorate the clinical and anatomical sequelae of ischemia.

Trials contemplated in which a rodent stroke model is used. In this model, the middle cerebral artery (MCA) is occluded by heat coagulation in adult Sprague-Dawley rats. These animals are then sacrificed after various intervals over a period of 14 days (Hillhouse et al., Neurosci. Lett. 249:177 [1997]). The brains are sectioned and the infarct volume and brain edema assessed, the levels of IL-1$\beta$, TNF-$\alpha$, and IL-6 mRNA levels are measured by RT-PCR in the infarct itself, in the region surrounding the infarct, and areas not affected by ischemia (Sharma and Kumar, supra). In an initial study the animals are treated daily (oral administration) with the PPAR$\gamma$ agonists indomethacin (2 mg/kg), docosahexanoic acid (100 mg/kg), Troglitazone (10–50 mg/kg), or vehicle (control) for one week in advance of the experiment and throughout the post-ischemic period. Follow-up trials are also conducted in animals that are given PPAR$\gamma$ agonists immediately following MCA occlusion. The animals are monitored for the first 4 hours at hourly intervals, and the 72 hr period at 24 hour intervals.

C. Traumatic Brain and Spinal Cord Injury

Traumatic injury to the nervous system, including percussive and penetrating injury to the brain and spinal cord provokes local synthesis and secretion of proinflammatory cytokines. The elevated levels of cytokines have been shown to initiate and alter the pathological changes that accompany the traumatic injury. Specifically, the levels of TNF-$\alpha$, IL-1$\beta$, and IL-6 are found to be significantly increased following injury as a result of their release from astrocytes and microglia. Many of the secondary changes associated with traumatic injury to the nervous system have been linked to this immune-mediated secondary degenerative response.

In some embodiments of the present invention, the trials use a well established model of contusive injury to the spinal cord to determine the effects of PPAR$\gamma$ agonists in reducing cavity size and improving behavioral recovery from trauma. In one embodiment, these trials use the NYU Weight-Drop Device (See e.g., Constantini and Young, J. Neurosurg. 80:97 [1994]; and Basso et al., Exp. Neurol. 139:244 [1996]), which provides a model of direct injury that can lead to cystic cavitation. This device produces standardized and reproducible contusive injuries to the spinal cord with four levels of graded lesion severity. In these trials, adult Sprague-Dawley rats are divided into four groups and subjected to contusive spinal cord injury in each of the four severity grades. Control animals receive daily oral administration of vehicle only, while experimental groups receive daily oral doses of the PPAR$\gamma$ agonists docosahexanoic acid (100 mg/kg), Troglitazone (10–50 mg/kg), or indomethacin (2 mg/kg) beginning on the day of experimental injury. The behavioral recovery of the animals is evaluated each week for 6 weeks based on the Basso, Beattie, and Bresnahan scale (BBB Scale) on a 0–21 scale that monitors hindlimb function (Basso et al., supra). Several animals from each group are sacrificed at 24 hours, 48 hours, and weekly thereafter for histological evaluation and quantification of lesion size, cavity size, and axonal degenerative changes. Levels of the inflammatory cytokines TNF-$\alpha$, IL-1$\beta$, and IL-6 are evaluated by RT-PCR in the damaged area of the spinal cord, the area immediately surrounding the damage, and areas distant from the injury at 1, 14, and 42 days following injury.

D. Clinical Evaluation of PPAR$\gamma$ Agonists in Alzheimer's Disease Patients

The efficacy of PPAR$\gamma$ agonists is evaluated in clinical trials measuring the disease progression in affected patients. For example, in one set of trials, the n-3 fatty acid, docosahexanoic acid, and the thiazolidinedione, Troglitazone (Rezulin) are tested in a double blind, placebo controlled, and randomized trial.

The primary patient enrollment criteria include patients who have moderate severity Alzheimer's Disease (Clinical Severity=2) without other central nervous system diseases, are not taking psychoactive medication, and are residing at home. The rate of disease progression is evaluated by following the patients over a period of two years using both primary and secondary outcome measures. Clinical evaluations are performed at three month intervals. The primary outcome measures include the time of death, institutionalization, loss of ability to perform two of three basic daily activities as measured using the Blessed Dementia Scale (See e.g., Heun el al., Int. J. Geriatr. Psychiatry 13:368 [1998]), and severe clinical dementia (Clinical Dementia rating=3). Secondary outcome measures include measures of cognition (Mini-mental State Examination and Alzheimer's Disease Assessment Scale [See e.g., Rogers et al., Arch. Intern. Med. 158:1021 (1998)]), and behavior (Behavior Rating Scale for Dementia [See e.g., Heun et al., supra]) and function. Function is evaluated by performance of instrumental activities (e.g., remembering lists and handling money) and basic activities (e.g., eating, toilet use, and grooming).

Patients receive DHA (6 gm/day) orally. This dose has been shown to be well tolerated and extensive data on the metabolism of the fatty acid at this dosage has been documented (Nelson et al., Lipids 32:1137 [1997]). Troglitazone (Rezulin) is tested at a dose of 400 mg/day. This dosage is that recommended for diabetes indications, and the design of this disease progression trial has been validated in a previous study of Vitamin E effects on Alzheimer's disease (Sano el al., New Engl. J. Med. 336:1216 [1997]).

Additional methods for testing the efficacy of PPARγ agonists in animal and human trials are known in the art (See e.g., Johnson et al., Ann. Pharma. 32:337 [1998]; Loi et al., J. Clin. Pharmacol. 37:1038 [1997]; Suter et al., Diabetes Care 15:193 [1992]; Ogihara et al., Am. J. Hypertens. 8:316 [1995]; Iwamoto et al., Diabetes Care 19:151 [1996]; Iwamoto et al., Diabetes Care 14:1083 [1991]; Nolan et al., N. Engl. J. Med. 331:1188 [1994]; Antonucci et al., Diabetes Care 20:188 [1997]; and Ghazzi et al., Diabetes 46:433 [1997]) and are contemplated by the present invention.

III. Drug Screening and Molecular Regulation of Disease

The present invention provides novel regulatory sequences for controlling COX-2 expression, identifying factors that influence COX-2 expression (e.g., drug screening methods), and identifying and controlling signaling pathways responsible for disease states associated with the over- or under-expression of COX-2. In particular, the present invention provides methods and compositions that utilize the PPARγ enhancer identified during the development of the present invention. In addition to the inflammatory diseases and conditions described above, the methods and compositions of the present invention find use in a broad array of physiological and cellular events that are influenced by COX-2 expression including, but not limited to, hormone signalling, growth factor signalling, cancer (See e.g., Franzese et al., Melanoma Res. 8:323 [1998]), including colorectal cancer, vision (See e.g,. Camras et al., Opthamology 103, 1916 [1996]), sleep/wake cycle (See e.g., Scrammell et al., Proc. Natl. Acad. Sci., 95:7754 [1998]), platelet aggregation (See e.g., Wu, J. Formos, Med. Assoc. 95, 661 [1996]), luteolysis (See e.g., Tsai and Wiltbank, Biol. Reprod. 57, 1016 [1997]), cellular differentiation and development, rheumatoid and osteo-arthritis (Vane et al., Ann. Rev. Pharm. Tox. 38:97 [1998]), and hyperalgesia, allodynia, and hyperthermia (Kaufmann, et al., Prostaglandins 54:601 [1997]), among others.

Cyclooxygenase-2, the inducible form of the cyclooxygenase enzyme, is mainly responsible for the pathological effects of prostaglandins where rapid induction of the enzyme would occur in response to such agents as inflammatory agents, hormones, growth factors, and cytokines. Thus, a selective inhibitor of COX-2 will have similar antiinflammatory, antipyretic, and analgesic properties of a conventional non-steroidal antiinflammatory drug, and in addition would inhibit hormone-induced uterine contractions and have potential anti-cancer effects, but will have a diminished ability to induce some of the mechanism-based side effects (e.g., side effects caused by inhibition of COX-1). In particular, in preferred embodiments, such compounds have a reduced potential for gastrointestinal toxicity, a reduced potential for renal side effects, a reduced effect on bleeding times, and in some embodiments, possibly a lessened ability to induce asthma attacks in aspirin-sensitive asthmatic subjects.

Accordingly, it is an object of the present invention to provide assays (methods) and materials (compositions) suitable for the identification and evaluation of pharmacological agents that are potent inhibitors of COX-2 and COX-2 activity. It is also an object of the present invention to provide assays and materials to identify and evaluate pharmacological agents that preferentially or selectively inhibit COX-2 and COX-2 activity over COX-1 and COX-1 activity.

Disclosed below are exemplary assays suitable for the screening of compounds that are associated with PPARγ and COX-2 signalling pathways and cellular responses. Any candidate compound can be tested by these assays. The present invention is not meant to be limited to the use of the illustrated assays, as other assays known to those skilled in the art may also be used.

The basis of the assays of the present invention is the transcriptional regulation of cox-2 by PPARγ through a regulatory element comprising a portion of the 5'-regulatory region of the cox-2 gene. In particular, the present invention provides nucleic acid molecules containing a 2.4 kb portion of the human cox-2 promoter comprising a PPARγ-responsive regulatory element (SEQ ID NO:1), as shown in FIG. 18 (Genbank Accession No.: U20548). The present invention contemplates the use of larger and smaller portions of the cox-2 promoter, so long as they contain the PPARγ-responsive regulatory element of the present invention, or functional analogues thereof. Methods such as those disclosed herein or otherwise known in the art are used to identify an active fragment of the cox-2 promoter, which confers regulatory activity upon a linked gene. For example, deletion mutants of the 2.4 kb portion of the human cox-2 promoter discussed above are constructed and the remaining portion analyzed for the ability to confer regulatory activity (e.g., PPARγ-responsive regulatory activity) upon a linked gene. Methods for preparing portions of promoter, such as a 5' or 3' deletion or an internal deletion are well known in the art, and include, for example, the use of naturally occurring or engineered restriction sites, nuclease digestion, or oligonucleotide-directed "loop-out" mutagenesis. In addition, small portions of the cox-2 promoter are constructed by annealing complementary synthesis oligonucleotides. Promoter regions are, as desired, altered by mutation (e.g., site-directed mutagenesis) to identify regulatory regions by loss of activity. A modified cox-2 promoter or a modified active fragment thereof, containing a modification that does not alter its ability to confer regulatory activity on a linked gene is encompassed with the meaning of "cox-2 promoter."

The oligonucleotide sequences of the DNA constructs of the present invention comprise the PPARγ-responsive regulatory element alone, or can include additional flanking nucleotide sequences. The oligonucleotide sequence component of the DNA constructs of the present invention may also comprise multimers of two or more "units" of the PPARγ-responsive regulatory element. When used in the DNA construct, including a promoter and heterologous gene, according to the present invention, a multimer of the regulatory elements enhances the expression of the gene from the DNA construct in response to PPARγ or other signaling molecules.

The recombinant DNA construct, such as a reporter plasmid, according to the present invention, is constructed using conventional molecular biology, microbiology, and recombinant DNA techniques well known to those of skill in the art. Such techniques are explained fully in the literature, including Maniatis et al. (Maniatis et al., "Molecular Cloning: A Laboratory Manual" [1982]) and Ausubel (Ausubel, "Current Protocols in Molecular Biology," Wiley, N.Y. [1994]), the disclosures of which are herein incorporated by reference. Methods and compositions for constructing and using COX-2 expression vectors are described in U.S. Pat. No. 5,543,297, incorporated herein by reference in its entirety.

In some embodiments of the present invention, the recombinant DNA composition or constructs of the present invention comprise a heterologous gene which may be composed of any desired set of nucleotides. Examples of such heterologous genes include, but are not limited to, the structural genes for luciferase, β-galactosidase, chloramphenicol acetyl transferase, secreted placental alkaline phosphatase, human growth hormone, tPA, green fluorescent protein, and interferon. For a more extensive list of heterologous genes usable in the constructs and methods of the present invention, see Beaudet (Beaudet, Am. J. Hum. Gen. 37:386 [1985]).

Preferably, the heterologous gene comprises a reporter gene whose product is used to assess regulation of transcription via a promoter and a regulatory element/oligonucleotide sequence of the present invention. The expression of the reporter sequence results in the formation of a reporter product (e.g., protein) which is readily detectable. In one embodiment of the present invention, the presence of the reporter molecule is detected through the use of an antibody or an antibody fragment, capable of specific binding to the reporter molecule. In another embodiment, a reporter such as β-galactosidase or luciferase is assayed enzymatically or immunologically.

In some embodiments, the recombinant molecules of the present invention are introduced into appropriate host cells to produce reporter cells. Host cells that are suitable for COX-2 expression are described in U.S. Pat. No. 5,543,297. The host cells used in the screening assay herein generally are mammalian cells, and preferably are human cell lines. Cell systems other than mammalian may also be used in the screening assays, including, but not limited to, Drosophila (SL-2, Kc, or others) and yeast strains such as S. cerevisiae and S. pombe, as well as other cells (e.g., nematode cells).

The reporter cells are treated with a compound or sample suspected of containing a molecule capable of regulating (e.g., activating or repressing) a transcriptional regulatory protein (e.g., PPARγ). When the desired incubation is complete, cells are assayed for the presence or absence of reporter product. The level of reporter product, when compared with control samples, indicates the ability of the test compound to regulate transcription through the cox-2 PPARγ-sensitive regulatory element. Experiments are also conducted with varying levels of PPARγ (e.g., varied by introduction of a PPARγ expression vector, by introduction of proteins that heterodimerize with PPARγ and alter its ability to bind to regulatory elements, or by introduction of compounds that induce native PPARγ expression) in the presence or absence of known PPARγ agonists. Such experiments identify the ability of test compounds to stimulate or antagonize PPARγ-induced regulation of COX-2 expression.

Generally, the assays of the present invention detect agonists and antagonists of signaling molecules that induce gene transcription via activated or repressed regulatory proteins (eg., PPARγ). As used herein, agonists or antagonists of gene transcription include compounds that intervene at any point within the signaling pathway from interaction between the signaling molecule and a cell surface receptor through activation of one or more transcriptional regulatory proteins and binding of the same to DNA regulatory elements, the end result of which is modulation of cox-2 gene transcription. Further, as used herein, agonists and antagonists of gene transcription also include potentiators of known compounds with such agonist or antagonist properties.

In preferred embodiments, agonists are detected by contacting the transfected host cell with a compound or mix of compounds and, after a fixed period of time, determining the level of gene expression (e.g., the level of reporter product) within the treated cells. This expression level is then compared to the expression level in the absence of the compounds. The difference between the levels of gene expression, if any, indicates whether the compounds of interest agonize the activation of intracellular transcriptional regulatory proteins in an analogous fashion to a known agonist signaling molecule (e.g., a known PPARγ agonist). Further, the magnitude of the level of reporter product expressed between the treated and untreated cells provides a relative indication of the strength of the compound as an agonist of gene transcription via a transcriptional regulatory protein pathway.

Alternatively, such a transfected host cell is used to identify antagonists of known agonists. In such preferred embodiments of these assays, the compound or compounds of interest are contacted with the host cell in conjunction with one or more known agonists held at a fixed concentration. The extent to which the compounds depress the level of gene expression in the host cell below that observed in the host cell in the absence of compounds, but in the presence of known agonist, provides an indication and relative strength of the antagonist properties of such compounds.

In some embodiments of the present invention, the screening assays are conducted in vivo. Animals such as mice can be used both as a primary screening vehicle in which compounds can be administered and parameters such as feeding, weight, levels of cytokine mRNA (e.g., TNF-α, IL-1β, and IL-6 mRNA levels), levels of COX-2 mRNA or protein production, or COX-2 activity levels (See e.g., U.S. Pat. No. 5,543,297) can be measured along with other appropriate controls to effectively assess the changes in COX-2 protein, mRNA, or activity. In alternative embodiments, a reporter gene or cox-2 cDNA (Genbank Accession Nos. AF044206, U20548, and U04636) operably linked to the cox-2 PPARγ-responsive 5'-regulatory region is introduced into animals utilizing standard transgenic practice, resulting in expression of the foreign DNA.

For example, in one embodiment of the present invention, transgenic mice are produced by injecting fertilized eggs with a construct containing a desired heterologous reporter gene under the regulatory control of the 2.4 kb portion of the human cox-2 promoter described above. The construct is microinjected into fertilized mouse eggs by the procedure of Brinster et al. (Brinster et al., Proc. Natl. Acad. Sci., 82:4438 [1985]). Transgenic animals are treated with test compounds using any desired administration method and tissues are harvested and tested for reporter gene expression to determine the ability of the test compound to alter expression compared to control animals that are not given the test compound. Agonists and antagonists are identified by their ability to increase or decrease reporter expression utilizing the PPARγ-sensitive regulatory element.

Thus, the present invention provides methods and compositions to assay for agonists and antagonists of cox-2 gene transcription utilizing the PPARγ-sensitive regulatory element of the DNA constructs and transfected host cells of the present invention. Further, the agonist and antagonist compounds discovered utilizing these methods and compositions can serve as pharmaceutical agents in the intervention of various COX-2 regulatory functions. In addition to the PPARγ agonists described above, these compounds find use in methods whereby the compounds are introduced into cells of a subject that are capable of expressing cox-2, and regulate cox-2 expression and the associated physiological functions. As desired, the compounds may be introduced along with compounds that stimulate or provide PPARγ expression if PPARγ is not otherwise sufficiently expressed in the cells (e.g., PPARγ expression constructs and agents that stimulate PPARγ expression). For example, in cells that are diseased due to undesired COX-2 expression, the therapeutic compounds of the present invention are introduced to facilitate PPARγ-induced repression of COX-2 expression. Indeed, the present invention provides a heretofor unrecognized means to target COX-2 expressing cells with compounds that regulate COX-2 expression through a PPARγ-associated mechanism.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); μM (micromolar); mol (moles); mmol (millimoles); μmol (micromoles); nmol (nanomoles); pmol (picomoles); g (grams); mg (milligrams); μg (micrograms); ng (nanograms); l or L (liters); ml (milliliters); μl (microliters); cm (centimeters); mm (millimeters); μm (micrometers); nm (nanometers); ° C. (degrees Centigrade); Sigma (Sigma Chemical Co., St. Louis, Mo.); and The following materials and protocols were used in the Example below.

A. Materials

The anti-phosphotyrosine antibody 4G10 was from Upstate Biotechnology Incorporated (Lake Placid, N.Y.). Anti-COX-2 antibody was from Transduction Laboratories (Lexington, Ky.). Anti-GFAP antibody was from the Accurate Chemical & Scientific Corporation (Westbury, N.Y.). Goat anti-mouse F(ab)$_2$ was obtained from Cappel (West Chester, Pa.). Affinity-purified horseradish-peroxidase conjugated goat anti-mouse and goat anti-rabbit antibodies were purchased from Boehringer Mannheim (Indianapolis, Ind.). Peptides corresponding to amino acids 25–35 and 1–40 of human β-amyloid were purchased from Bachem (Philadelphia, Pa.). β-amyloid peptides were resuspended in sterile dH$_2$O. Fibrillar β-amyloid 1–40 was prepared by reconstitution of the lyophilized peptide in sterile distilled water, followed by incubation for 1 week at 37° C. LPS, TPA, and Concanavalin A (Con A) was purchased from Sigma. Ciglitazone was obtained from Biomol (Plymouth Meeting, Pa.). DHA and prostaglandin J$_2$ were obtained from Calbiochem (San Diego, Calif.).

B. Tissue Culture

THP-1 cells were grown in RPMI-1640 (Whittaker Bioproducts, Walkersville, Md.) supplemented with 10% heat-inactivated fetal calf serum (FCS), $5 \times 10^{-5}$ M 2-mercaptoethanol, 5 mM HEPES, and 2 μg/ml gentamicin in 5% CO$_2$. Microglial and astrocyte cultures were derived from postnatal day 1–2 mouse brain (C57B1/6J) as previously described (McDonald et al., J. Neurosci. 18:4451 [1997]). Astrocytes were recovered after harvesting of microglia and serially passaged to enrich for astrocytes. Neurons were cultured from cortices of E17 mice (C57B1/6J). Meninges-free cortices were isolated and digested in 0.25% trypsin, 1 mM EDTA for 15 min, 37° C. The trypsin was inactivated with DMEM containing 20% heat inactivated FCS. Cortices were transferred to Neurobasal media with B27 supplements, triturated and plated onto poly-L-lysine (0.05 mg/ml) coated tissue culture wells. Neurons were grown in Neurobasal media ($4.0 \times 10^4$/24-well tissue culture plate) with B27 supplement for 5–7 days in vitro before use.

C. Cell Stimulation

THP-1 cells and microglia were stimulated by first removing their respective median replacing it with Hank's Balanced Salt Solution (HBSS) for 30 minutes at 37° C. prior to stimulation. Cells were stimulated in suspension (5–10× $10^6$ cells/200 μl HBSS) or by plating onto bound peptides (48 pmole/mm$^2$). Bound peptides were prepared as described previously (Lagenaur and Lemmon, Proc. Natl. Acad. Sci. 84:7753 [1987]). Briefly, tissue culture wells were coated with nitrocellulose and peptides were added to the coated wells and allowed to dry. The wells were then incubated with sterile 3% BSA in dH$_2$O for 1 hour to block cell interactions with nitrocellulose. The BSA was removed and THP-1 cells were added in HBSS for 10 minutes. To condition the media, THP-1 cells ($1.8 \times 10^4$) were added to wells containing the bound peptides in 48-well tissue culture dishes in 0.25 ml of Neurobasal media for 48 hours with or without drugs.

D. Neurotoxicity Studies

Neuronal toxicity experiments with THP-1 monocytes involved addition of 0.25 ml of conditioned media, as described above. The media was collected, centrifuged to pellet non-adherent cells, and added directly to neural cultures (5–7 days in vitro) for 72 hours. All conditions were conducted in duplicate and a counting grid was placed over the wells to count neuron numbers from eight identical fields for each condition. Neuron numbers were averaged for each condition to evaluate neuron survival.

E. Western Blotting

Cells were lysed in 200 μl ice-cold RIPA buffer (1% Triton, 0.1% SDS, 0.5% deoxycholate, 20 mM Tris (pH 7.4), 150 mM NaCl, 10 mM NaF, 1 mM Na$_3$VO$_4$, 1 mM EDTA, 1 mM EGTA, 0.2 mM PMSF) and insoluble material was removed by centrifugation at 10,000×g at 4° C. for 10 min. Protein concentrations were quantitated by the method of Bradford (Bradford, Anal. Biochem. 72:248 [1976]). Proteins were resolved by 7.5% SDS-PAGE and Western blotted with primary antibody: 4G10 (1:2000) or COX-2 (1:250) overnight at 4° C. Antibody binding was detected via enhanced chemiluminescence (Pierce, Rockford, Ill.).

F. Cyclooxygenase-2 Expression

THP-1 monocytes or RAW 264.7 murine macrophages were incubated with TPA (100 nM), LPS, or fibrillar Aβ25–35 for 18 hours in RPMI medium containing 5% FCS in the presence or absence of the various drugs. The cells were lysed in RIPA buffer and aliquots of the cellular lysates were resolved by SDS-PAGE, transferred to PVDF membranes and probed with an antibody to COX-2.

G. IL-6 and TNF-α Promoter Assays

A human IL-6-luciferase reporter construct containing the upstream promoter sequences (-1160-+14) coupled to luciferase was transfected into THP-1 cells using DEAE-dextran, together with a β-galactosidase reporter construct to control for transfection efficiency. The human TNF-α reporter construct comprised sequences 1.2 kb of 5' upstream promoter sequence linked to luciferase. The cells were transfected and 48 hrs later stimulated in serum-free RPMI for 6 hours using 40 μM Aβ or 1 μg/ml LPS in the presence or absence of drugs, lysed, and luciferase activity was measured.

H. Cyclooxygenase-2 Promoter Assays

A plasmid bearing 2.3 kb of the 5' flanking region of the human cyclooxygenase-2 gene couple to a luciferase reporter (a gift of Dr. Peter Polgar at Boston University) was used to electroporate THP-1 monocytes (40 μg DNA/$10^7$ cells). A SV40 driven-β-galactosidase vector was cotransfected to allow evaluation of transfection efficiency. Cells were then incubated in the absence or presence of the indicated agents for the last 18 hours of the incubation. The cells were lysed 48 hours after transfection and luciferase activity was measured.

EXAMPLE 1

PPARγ Agonists Effects on Aβ-Stimulated Intracellular Signaling Pathways

This example demonstrates that Aβ-stimulated intracellular signaling pathways are unaffected by PPARγ agonists. Exposure of THP-1 monocytes or primary microglial cells to fibrillar forms of Aβ resulted in the stimulation of protein tyrosine phosphorylation as a consequence of the activation of the tyrosine kinases Lyn, Syk, FAK, and Pyk2 (Burridge and Chrzanowska, Ann. Rev. Cell Dev. Biol. 12:463 [1996]; Ghazizadeh et al., J. Biol. Chem. 269:8878 [1994]; Kiener et al., J. Biol. Chem. 268:24442 [1993]; and Lev et al., Nature 376:737 [1995]) as shown in FIG. 1. In FIG. 1, THP-1 cells were stimulated in vehicle only (c) or with βA25–35 (40 μM, 2 min) or Con A (60 μg/ml, 5 min, positive control). Increased tyrosine kinase activity in THP-1 cells stimulated by β-amyloid was monitored by immunoprecipitating tyrosine phosphorylated proteins using the anti-phosphotyrosine antibody, PY20. The immunoprecipitated proteins were incubated in [$^{32}$P]ATP and allowed to autophosphorylate to visualize activated tyrosine kinases and their substrates. The figure shows an autoradiogram of the proteins resolved by SDS-PAGE.

Figure 2:
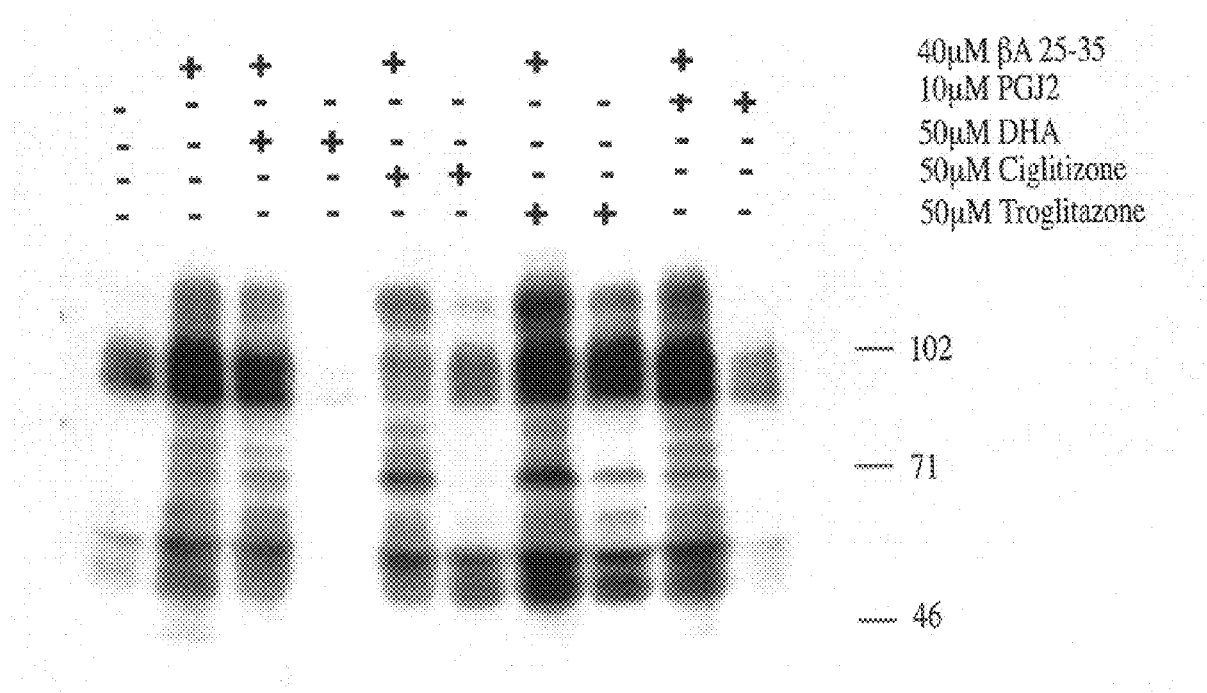
FIG. 2 shows the affects of PPARγ agonists on the activation of the tyrosine kinase signaling cascade as examined by Western blot of cell lysates using an anti-phosphotyrosine antibody.
Figure 3E:
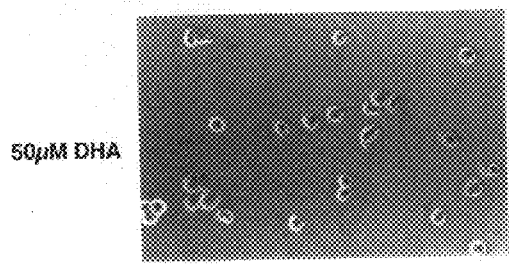
Figure 3F:
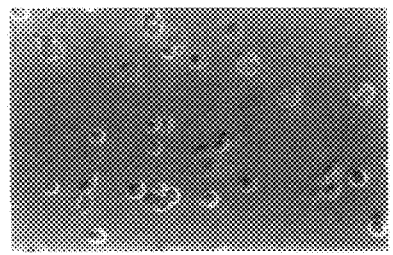
Figure 3G:
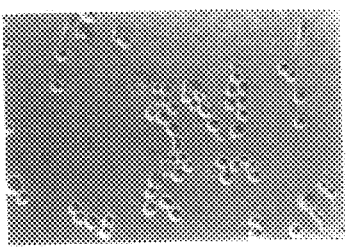
Figure 3H:
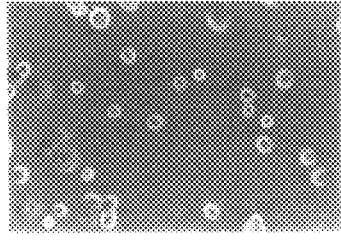
Figure 3I:
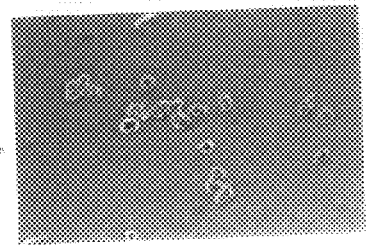
Figure 3J:
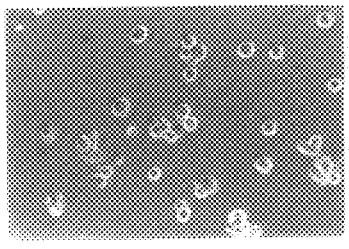

The ability of PPARγ agonists to affect the activation of the kinases and elements of the signal transduction apparatus mediating the responses of these cells to Aβ was tested. The PPARγ agonists, PGJ$_2$, DHA, ciglitazone, and troglitazone, did not significantly alter the induction of protein tyrosine phosphorylation following Aβ exposure as shown in FIG. 2. In this figure, the effect of PPARγ agonists on the activation of the tyrosine kinase signaling cascade was examined by Western blot of cell lysates using the anti-phosphotyrosine Ab, 4G10 following 24 hour incubation of the cells with vehicle only (DMSO) or 10 μM PGJ$_2$, 50 μM DHA, 50 μM ciglitazone, or 50 μM troglitazone. These data demonstrate that PPARγ agonists do not interact with the principal catalytic components of the signal transduction cascades linked to the inflammatory responses in these cells.

EXAMPLE 2

PPARγ Agonist Effects on Macrophage Differentiation

This example demonstrates that PPARγ agonists prevent the differentiation of THP-1 cells into macrophages. Monocytes undergo a morphological and biochemical differentiation into a macrophage phenotype following exposure to phorbol ester or other activating stimuli (Tsuchiya et al., Cancer Res. 42:1530 [1982]). The phenotypic conversion of THP-1 cells into macrophages was stimulated by a 48 hour exposure of the cells to TPA (100 nM) as shown in FIGS. 3A–J. The ability of PPARγ agonists to prevent TPA induced differentiation was monitored morphologically. Cells were incubated with (FIG. 3A) vehicle only (control; DMSO, ethanol) or (FIG. 3B) 100 nM TPA for 48 hours with or without PPARγ agonists: (FIGS. 3C,D) 10 μM PGJ$_2$, (FIGS. 3E,F) 50 μM DHA, (FIGS. 3G,H) 50 μM ciglitazone, and (FIGS. I,J) 50 μM troglitazone. As shown in this figure, concomitant exposure of the cells to TPA and PPARγ agonists PGJ$_2$, DHA, ciglitazone, and troglitazone blocked the differentiation of the cells. These data provide direct evidence that PPARγ agonists act to inhibit a broad range of cellular activities that participate in the differentiation of these cells. Moreover, these findings are consistent with a role for these agents acting as anti-inflammatory agents through their capacity to block the generation of a reactive phenotype in these cells.

EXAMPLE 3

PPARγ Agonist Effects on Microglial-mediated Activation of Astrocytes

This example demonstrates that PPARγ agonists block microglial-mediated activation of astrocytes. Astrogliosis and the acquisition of a ramified, "activated" morphology is observed in a number of CNS diseases and in response to both acute and chronic brain insults. A primary response of astrocytes in these settings is the elevated expression of the intermediate filament protein, glial fibrillary acidic protein (GFAP), which servers as the canonical marker of astrocyte activation. The conditioned medium contains a number of proinflammatory secretory products elaborated by the monocytes following their activation by Aβ fibrils. This culture system provides a model for investigation of astrogliosis observed in Alzheimer's disease as well as a number of CNS disorders in which astrocyte reactivity plays a pivotal role.

FIG. 4 shows the ability of PPARγ agonists to prevent β-amyloid stimulated conditioned media from THP-1 cells to induce a reactive astrocyte morphology in culture. THP-1 cells were stimulated for 48 hours by plating alone or onto surface bound βA 25–35 (48 pmole/mm$^2$) in the presence of vehicle (DMSO) or 10 μM PGJ$_2$. Media was collected from (FIG. 4A) media only wells, (FIG. 4B) βA 25–35 stimulated THP-1 cell cultures, (FIG. 4C) βA 25–35 stimulated TBP-1+10 μM PGJ$_2$ cell cultures, (FIG. 4D) 10 μM PGJ$_2$ only wells, (FIG. 4E) wells with surface bound βA only, and (FIG. 4F) THP-1 cell only cultures. The conditioned medium was then added to purified mouse astrocyte cultures for 72 hours. Cultures were fixed and stained for glial fibrillary acidic protein (GFAP).

As shown in FIG. 4, exposure of astrocytes to conditioned medium from untreated THP-1 cells or astrocytes and direct exposure to fibrils did not lead to detectable differences from control cultures as evaluated by their morphology or GFAP expression. However, conditioned medium from activated, Aβ-treated THP-1 cells provoked a dramatic increase in GFAP immunoreactivity and development of a ramified morphology reflective of the astrocyte activation. Importantly, THP-1 cells that were treated simultaneously with Aβ and the PPARγ agonist PGJ$_2$ were similar in appearance to control cultures. These observations provide evidence that the PPARγ agonists inhibit the production of microglial secretory products that are responsible for activation of astrocytes.

EXAMPLE 4

PPARγ Agonists Effects on Monocyte-mediated Neurotoxicity

This example demonstrates that PPARγ agonists prevent monocyte-mediated neurotoxicity. Microglial activation is accompanied by their secretion of numerous acute phase and proinflammatory products which typify macrophage responses in the periphery. Numerous studies have described that ability of microglial lineage cells to generate neurotoxic products in response to treatment with Aβ peptides (See e.g., Banati et al., Glia 7:111 [1993]; Giulian, Glia 7:102 [1993]; Giulian et al., Neurochem. Int. 27:119 [1995]; and Giulian et al., J. Neurosci. 16:6021 [1996]). A variety of the microglial secretory products have been reported to be toxic to neurons including cytokines, chemokines, reactive oxygen and nitrogen species as well as undefined neurotoxic components (Brown et al., Nature 380:345 [1996]; Ii et al., Brain Res. 720:93 [1996]; and Kretzschmar et al., J. Neur. Transm. 50 [1997]). The release of these neurotoxic products represent the outcome of a coordinated program of biological responses mediating a proinflammatory response.

The experiments in this Example employed a tissue culture model system in which highly purified populations of primary cortical neurons were cultured in conditioned media from THP-1 cells or primary microglia to evaluate and quantitate the elaboration of neurotoxic and proinflammatory products. Specifically, purified cultures of mouse cortical neurons (E16, $4.0 \times 10^4$ neurons/well used 5–7 days in vitro) were cultured alone, or in the presence of conditioned media from THP-1 cells ($1.8 \times 10^4$ THP-1 cells/condition). THP-1 cells were stimulated for 48 hours by plating into tissue culture wells only, or wells coated with βA 25–35 (48 pmole/mm$^2$) in the presence of DMSO vehicle (control) or PPARγ agonists. The conditioned medium from media only wells, THP-1 cell only cultures, surface bound βA 25–35 only wells, drug only wells, βA+THP-1 cell cultures, and βA+THP-1 cell+drug cultures, was added to mouse cortical neuron cultures for 72 hours. Neurons were then fixed and stained for neuron specific MAP2 protein, and counted to quantitate neuronal survival.

Figure 5:
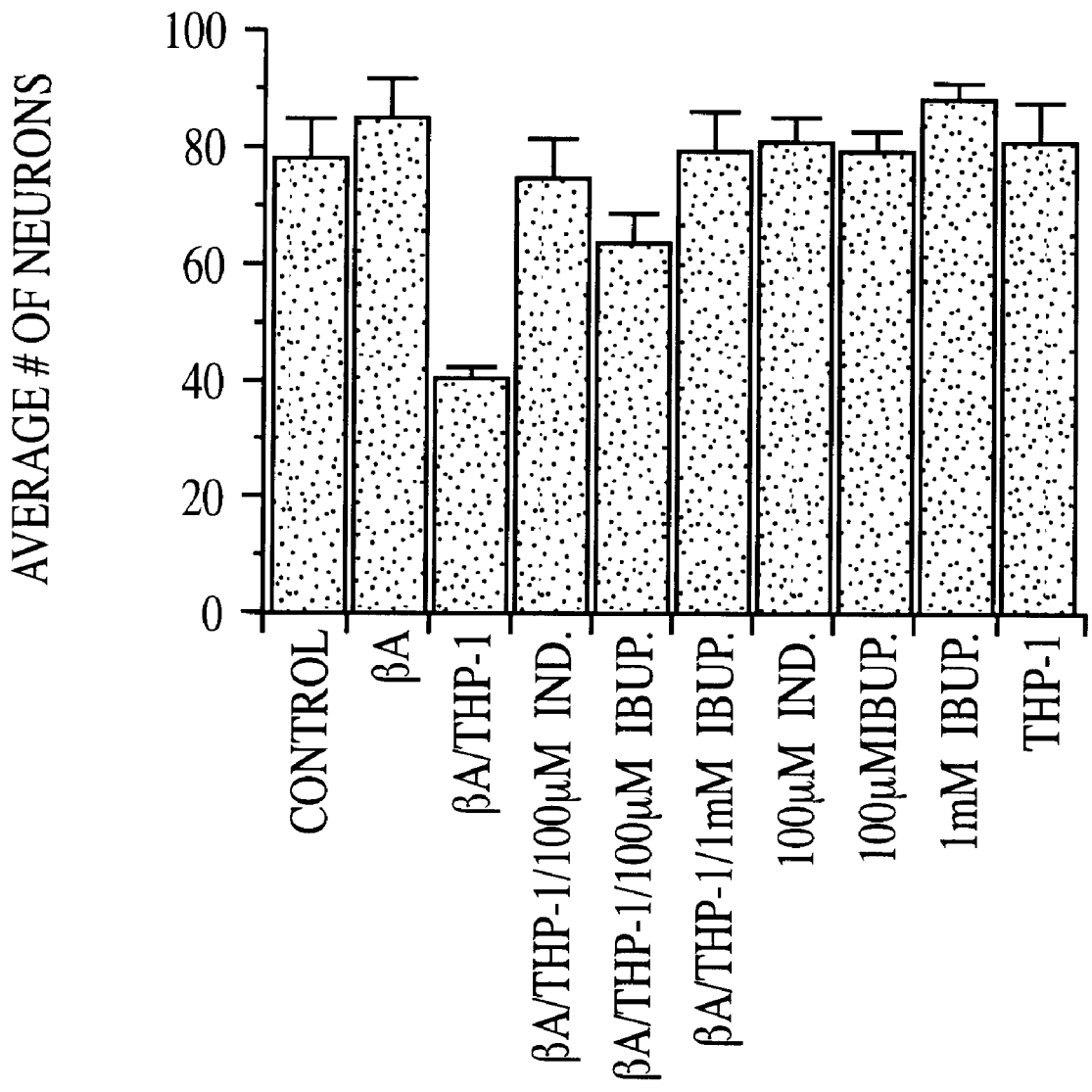
FIG. 5 shows a graph of cell survival upon treatment of THP-1 cells with the indicated compounds.

Conditioned medium from untreated THP-1 exhibited little or no neurotoxicity. However, the conditioned medium from THP-1 cells exposed to fibrillar Aβ was highly neurotoxic, killing the majority of the neurons within 72 hours. If the THP-1 monocytes were exposed to Aβ in the presence of the NSAIDs and PPARγ agonists ibuprofen (100 μM, 1 mM) or indomethacin (100 μM), the production of neurotoxins was inhibited, as shown in FIG. 5.

Figure 6:
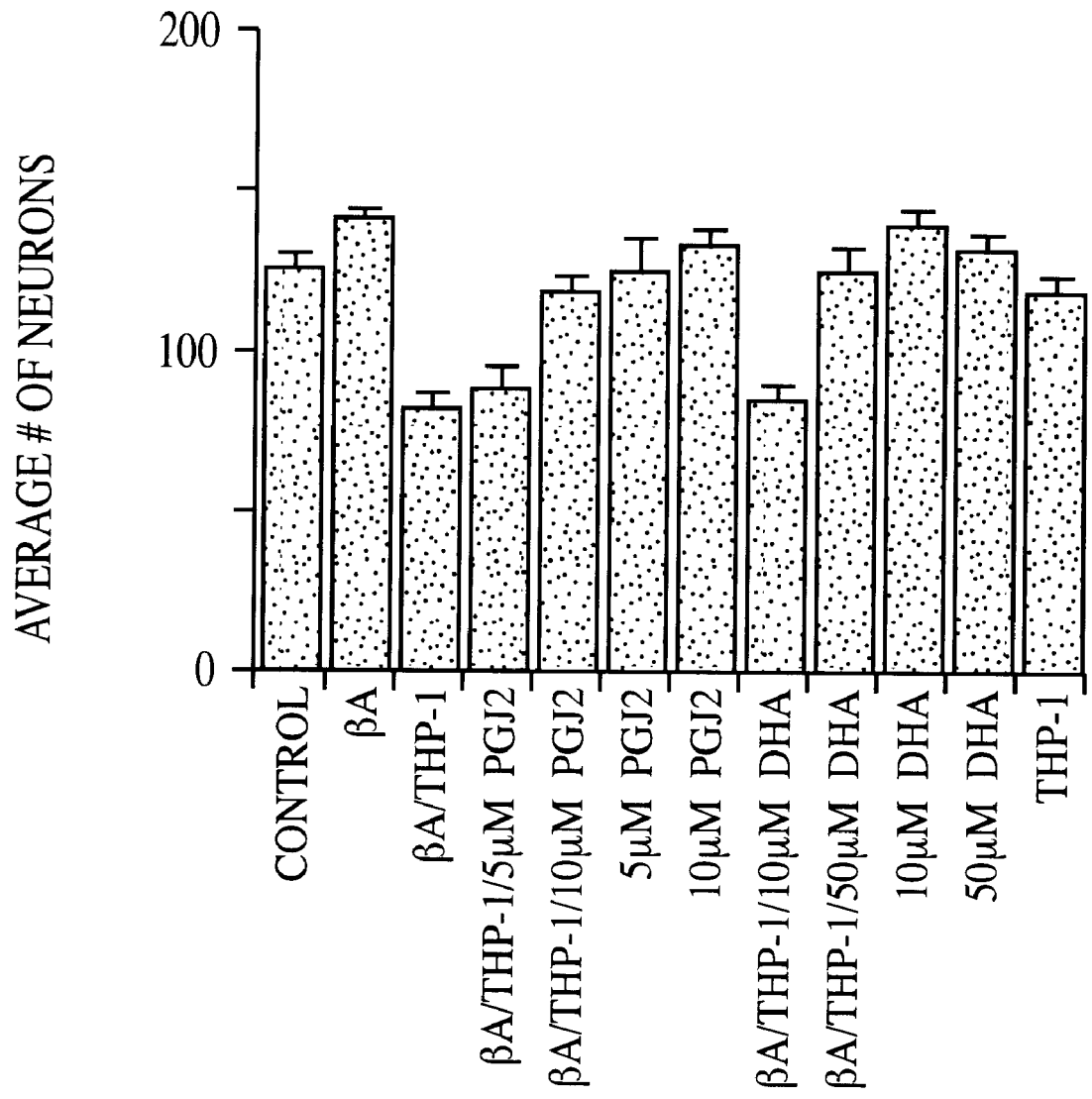
FIG. 6 shows a graph of cell survival upon treatment of THP-1 cells with the indicated compounds.
Figure 7:
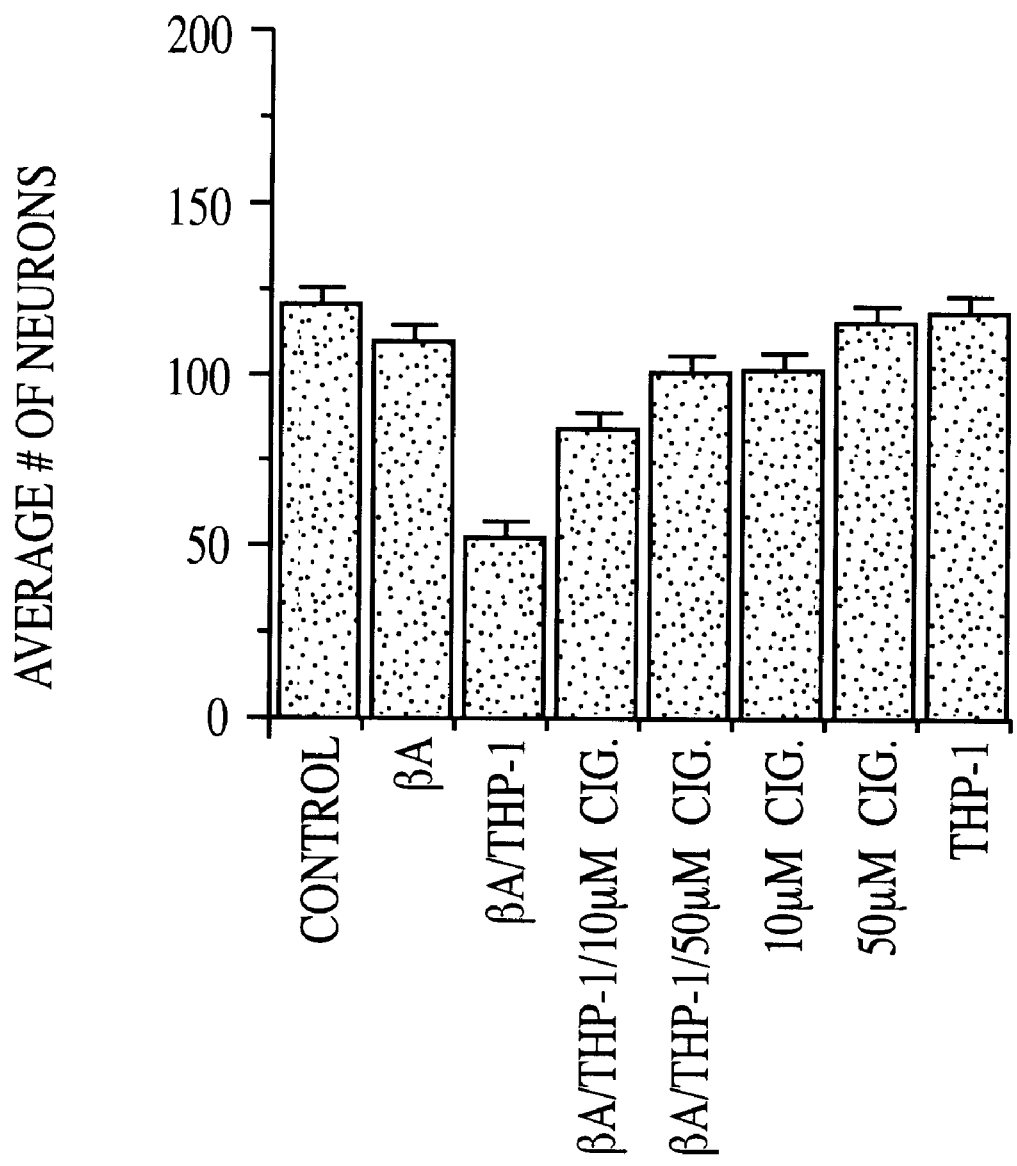
FIG. 7 shows a graph of cell survival upon treatment of THP-1 cells with the indicated compounds.
Figure 8:
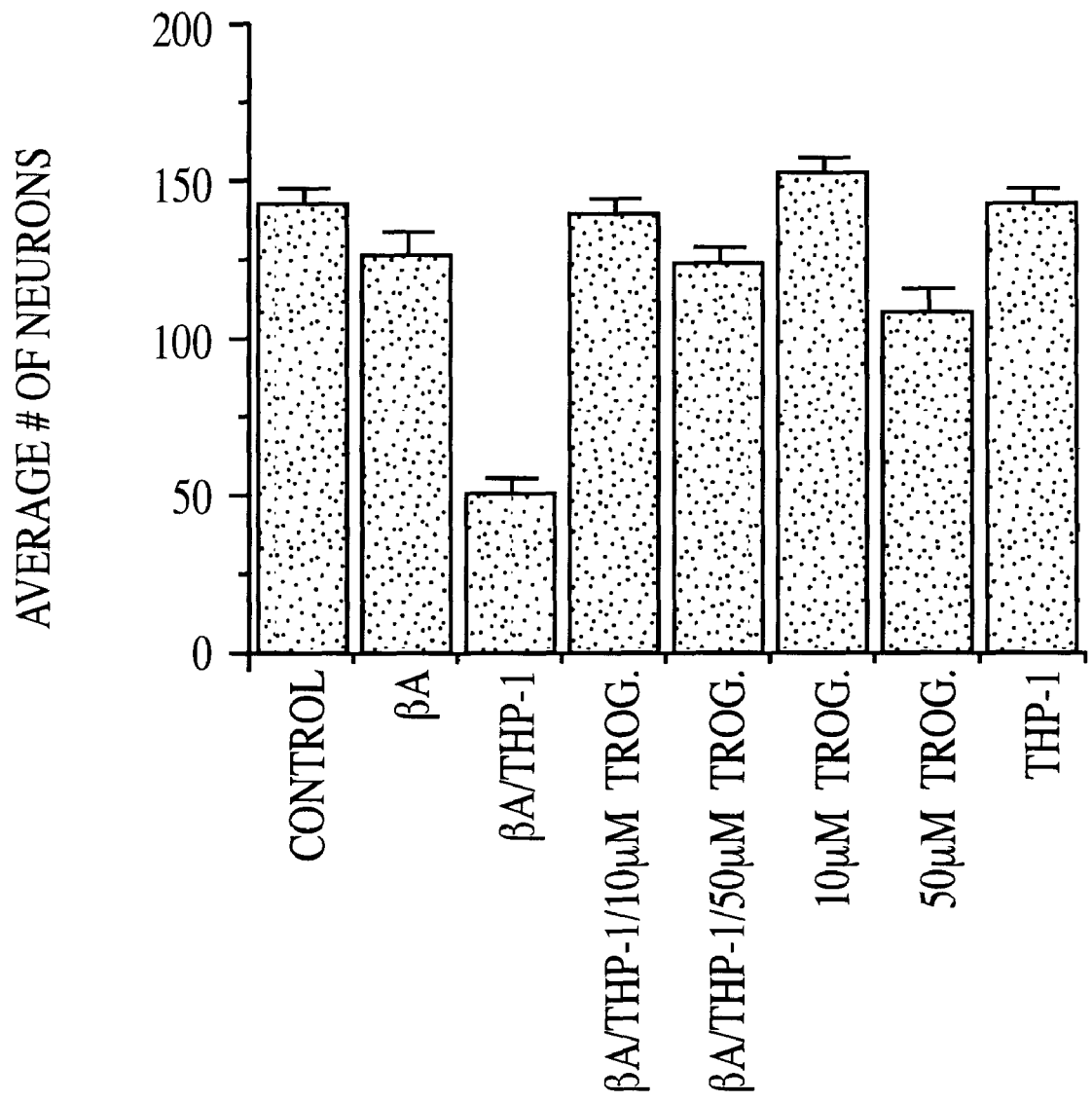
FIG. 8 shows a graph of cell survival upon treatment of THP-1 cells with the indicated compounds.

Similarly, the PPARγ agonists PGJ$_2$ (5 μM, 10 μM) and DHA (10 μM, 50 μM) (FIG. 6) and the thiazolidinediones, ciglitazone (10 μM, 50 μM) (FIG. 7) and troglitazone (10 μM, 50 μM) (FIG. 8), also arrested the production of neurotoxins. These data demonstrate that a variety of PPARγ agonists act to suppress the elaboration of proinflammatory neurotoxic products from activated monocytes/macrophages.

EXAMPLE 5

PPARγ Agonists Effects on Interleukin-6 and TNF-α Expression

Figure 9A:
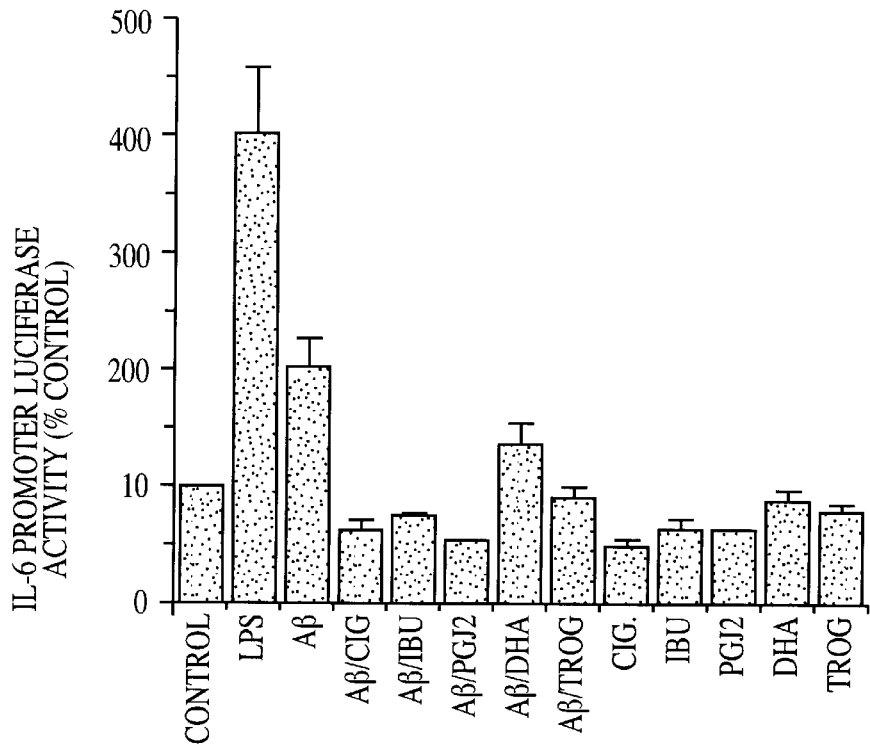
FIG. 9A shows a graph of IL-6 promoter activity in response to the indicated compounds.
Figure 9B:
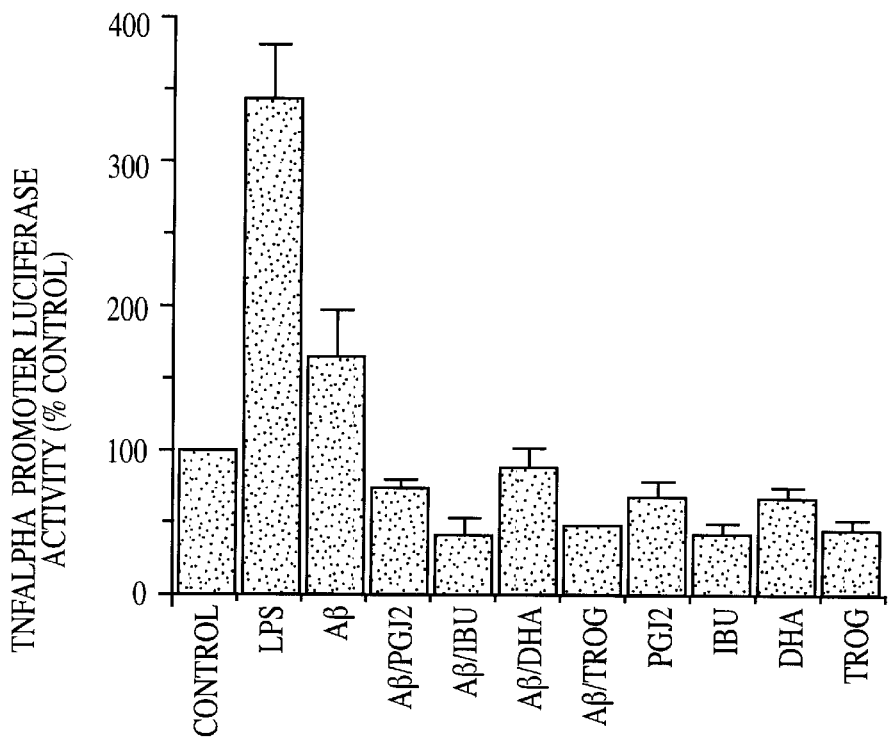
FIG. 9B shows a graph of TNF-α promoter activity in response to the indicated compounds.

This example demonstrates that PPARγ agonists inhibited interleukin-6 and TNF-α expression. One consequence of microglial activation by Aβ or other immune stimuli is the stimulation of cytokine production. The experiments in this Example tested whether PPARγ agonists would affect the activity of the promoters of the human IL-6 and TNF-α genes. These experiments employed a luciferase-linked reporter to the promoter elements of the human genes. THP-1 cells were transiently transfected with IL-6 luciferase reporter or TNF-α reporter constructs and assayed for promoter activity 48 hours later. The cells were cotransfected with a β-galactosidase-reporter construct to control for transfection efficiency. During the last 6 hours, the cells were incubated with LPS (1 μg/ml) or Aβ25–35 (40 μM) in the presence or absence of troglitazone (50 μM), ciglitazone (50 μM), DHA (50 μM), PGJ$_2$ (10 μM), or ibuprofen (1 mM). Experiments were conducted in duplicate, with reported data representing the average of the determinations. LPS and Aβ-treatment of THP-1 cells resulted in the stimulation of promoter activity of both cytokine genes, consistent with the in vivo effect of these agents on cytokine production, as shown in FIGS. 9A and 9B. Incubation of THP-1 cells with the natural PPARγ agonists PGJ$_2$ and DHA resulted in inhibition of promoter activity. Similarly, the thiazolidinediones, troglitazone and ciglitazone, as well as ibuprofen, also blocked expression of the reporter. These data demonstrate that a diverse range of PPARγ agonists efficiently suppressed expression of the IL-6 and TNF-α genes.

EXAMPLE 6

PPARγ Agonists Effects on Cyclooxygenase-2 Expression

Figure 10A:
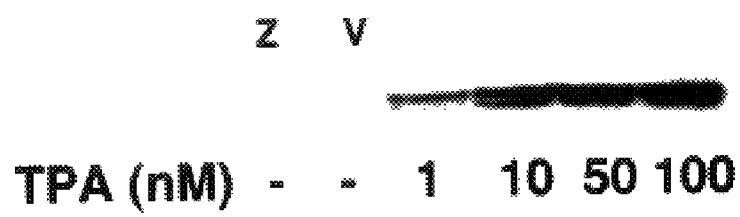
FIG. 10A shows cyclooxygenase-2 expression as assessed by Western analysis of cell lysates using a COX-2-specific antibody upon treatment with phorbol ester.
Figure 10B:
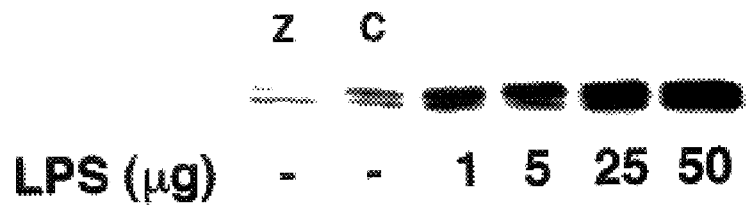
FIG. 10B shows cyclooxygenase-2 expression as assessed by Western analysis of cell lysates using a COX-2-specific antibody upon treatment with LPS.

This example demonstrates that PPARγ agonists block cyclooxygenase-2 expression. Specifically, this example demonstrates that cyclooxygenase-2 (COX-2) is inducibly expressed in response to a variety of immune stimuli. Treatment of THP-1 cells with phorbol ester (TPA) or LPS for 18 hours resulted in the induction of COX-2 expression in a dose-dependent manner, as shown in FIGS. 10A and 10B. In FIG. 10A, THP-1 monocytes were incubated in the presence of vehicle (v), or the indicated concentration (nM) of phorbol ester (TPA). Untreated cells are designated "z". In FIG. 10B, THP-1 monocytes were untreated (z) or incubated alone (c) or in the presence of vehicle (v), or the indicated concentration (nM) of LPS.

Figure 11A:
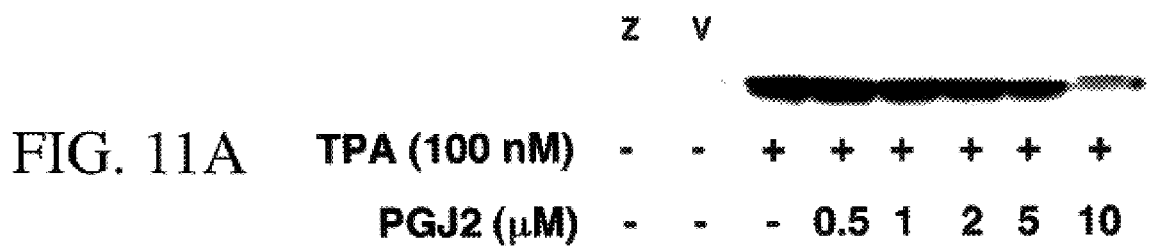
FIG. 11A shows cyclooxygenase-2 expression as assessed by Western analysis of cell lysates using a COX-2-specific antibody upon treatment with phorbol ester and PPARγ agonist.
Figure 11B:
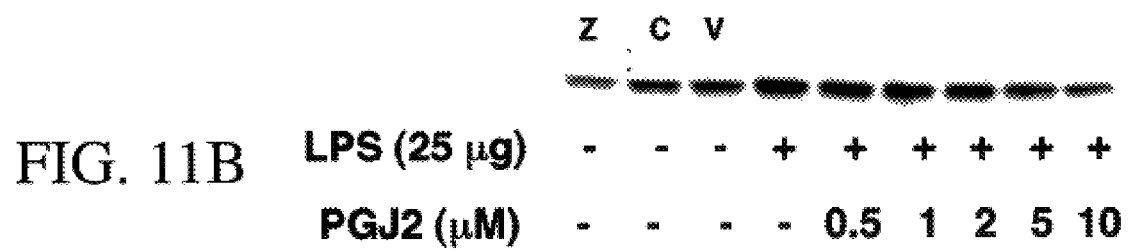
FIG. 11B shows cyclooxygenase-2 expression as assessed by Western analysis of cell lysates using a COX-2-specific antibody upon treatment with LPS and PPARγ agonist.

The TPA and LPS-induced COX-2 expression was inhibited by the PPARγ agonist PGJ$_2$ with near complete suppression of expression at a dose of 10 μM PGJ$_2$, as shown in FIGS. 11A and 11B. In FIG. 11A, THP-1 monocytes were incubated in the presence or absence of 100 nM TPA and the indicated concentration (μM) of PGJ$_2$. In FIG. 11B, THP-1 monocytes were incubated in the presence or absence of 25 μg of LPS and the indicated concentration (μM) of PGJ$_2$. Cyclooxygenase-2 expression was assessed by Western analysis of cell lysates using a COX-2-specific antibody.

Figure 12A:
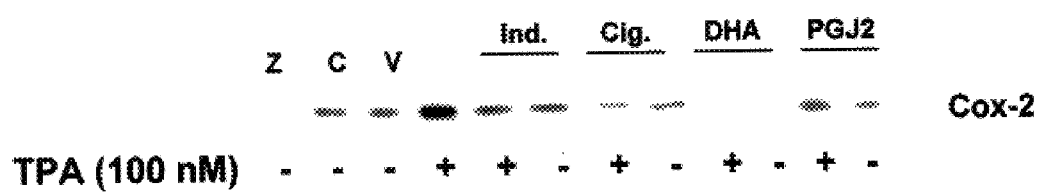
FIGS. 12A–B show cyclooxygenase-2 expression as assessed by Western analysis of cell lysates using a COX-2-specific antibody upon treatment with phorbol ester and the indicated PPARγ agonists.
Figure 12B:
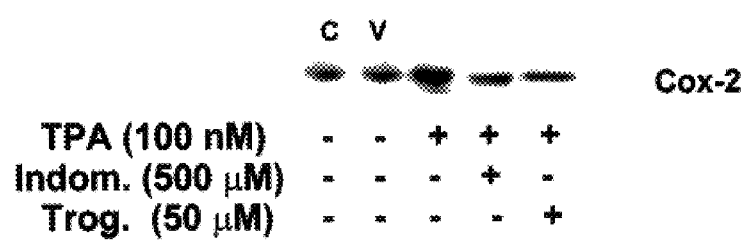

The PPARγ agonists, ciglitazone, troglitazone, DHA and indomethacin, also suppressed the TPA-stimulated COX-2 expression, as shown in FIGS. 12A and 12B. In these experiments, THP-1 monocytes were incubated in the presence or absence of 100 nm TPA for 18 hours. The PPARγ agonists indomethacin (1 mM), ciglitazone (50 μM), docosahexanoic acid (100 μM), and PGJ$_2$ (10 μM) (FIG. 12A) or indomethacin (500 μM) or troglitazone (50 μM) (FIG. 12B) were added to the cultures alone or in combination with TPA. COX-2 expression was monitored by Western analysis of cellular lysates and the blots probed with a anti-COX-2 specific antibody.

Figure 13A:
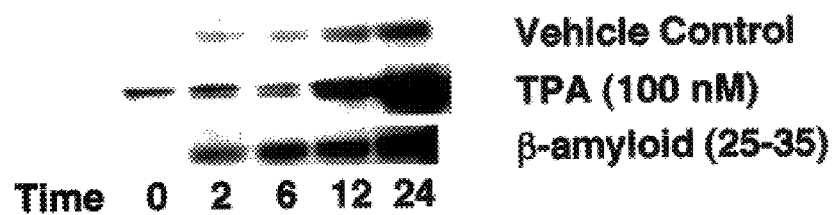
FIGS. 13A–B show cyclooxygenase-2 expression as assessed by Western analysis of cell lysates using a COX-2-specific antibody upon treatment with phorbol ester or β-amyloid in the presence or absence of PPARγ agonist.
Figure 13B:
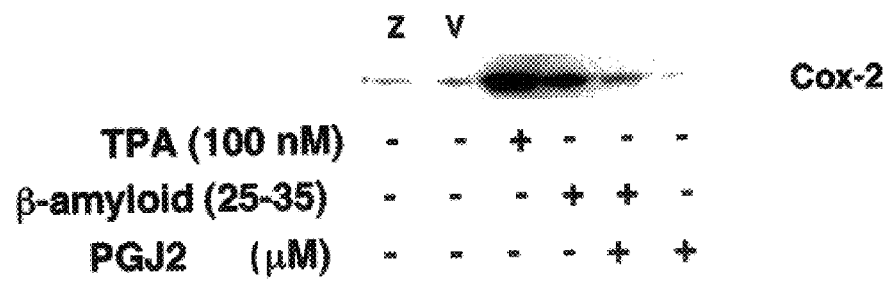

Aβ, like TPA, treatment of THP-1 cells resulted in the rapid induction of COX-2 expression which was sustained for up to 24 hours, as shown in FIG. 13A. In this Figure, THP-1 monocytes were incubated with vehicle (DMSO), TPA (100 nM) or Aβ25–35 fibrils for 0–24 hours. Co-incubation of the cells with a specific agonist of PPARγ, PGJ$_2$, dramatically inhibited COX-2 expression, as shown in FIG. 13B. In this Figure, the murine macrophage line, RAW 264.7, was incubated for 18 hours with phorbol ester (100 nM) or fibrillar Aβ (25–35) (40 μM) in the absence or presence of PGJ$_2$ (10 μM). COX-2 expression was monitored by Western analysis of cellular lysates and the blots probed with a anti-COX-2 specific antibody. These observations are of particular significance as they demonstrate that the present invention provides a novel therapeutic approach for suppression of COX-2 action in AD and other inflammatory disorders.

EXAMPLE 7

PPARγ Agonists Effects on COX-2 Promoter Activity

Figure 14:
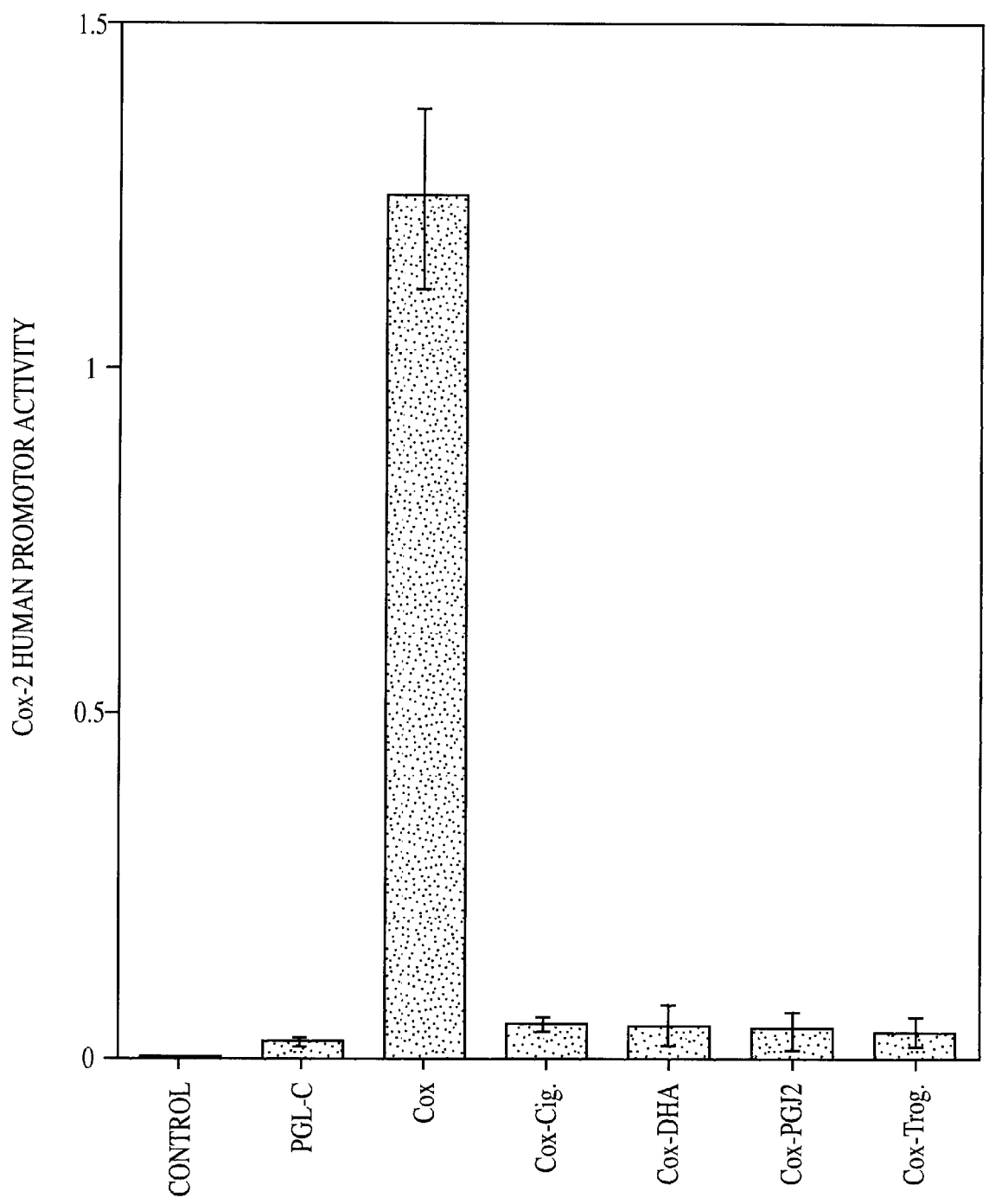
FIG. 14 shows human Cox-2 promoter activity in response to the indicated compounds.

This example demonstrates that PPARγ agonists inhibit COX-2 promoter activity. COX-2 promoter activity was assessed in THP-1 cells using a construct containing 2.4 kb of the human COX-2 promoter coupled to a luciferase reporter. The activity of the promoter was dramatically inhibited (approximately 90% inhibition) when the cells were treated with the PPARγ agonist $PGJ_2$. Similarly, the thiazolidinediones, ciglitazone and troglitazone arrested transcription from this promoter, as did DHA, as shown in FIG. 14. Specifically, THP-1 cells were transfected with a COX-2-luciferase reporter construct by electroporation. The cells were cotransfected with an SV-40-β-galactosidase plasmid to allow evaluation of transfection efficiency. The cells were incubated for 48 hours, lysed, and luciferase and β-galactosidase activity was measured. During the last 18 hours, the cells were incubated in the absence or presence of the indicated agents (Control=untransfected cells; PGL-C= vector control; COX=cells transfected with the COX-2-luciferase reporter; transfected with the COX-2-luciferase reporter cells and incubated for 18 hours with $PGJ_2$ [10 μM], troglitazone [50 μM], ciglitazone [50 μM], or DHA [50 μM]). Data represent the mean of duplicate determinations in two independent experiments (+/− SEM). These data verify that the regulated expression of COX-2 expression by PPARγ is a direct consequence of the action of these drugs on cis acting promoter elements in the COX-2 gene.

EXAMPLE 8

PPARγ Agonists Effects on Central Nervous System Injury

Astrocytes were isolated from P0 Sprague-Dawley rat pups using standard techniques, seeded at a density of 50,000 cells per well in 24-well tissue culture plates on glass coverslips coated with poly-L-lysine (0.1 mg/ml) and laminin (5 μg/ml), and allowed to reach confluency (1–3 days) in DMEM-F12 culture medium supplemented with 10% fetal calf serum. Thioglycollate-elicited peritoneal macrophages were isolated from adult Sprague-Dawley rats after 3 days and introduced into the astrocyte cultures at a density of 100,000 cells per well. Non-activated macrophage were seeded in culture media only, while activated macrophages are introduced with 0.5 mg/ml Zymosan, a potent macrophage activator. Zymosan is a cell wall particle derived from S. cerevisiae and is composed of alpha-mannan and beta-glucan residues (Lombard et al., J. Immunol. Methods 174:155 [1994]). Phagocytosis of Zymosan involves the MFR mannose receptor and beta-glucan receptor (Czop, Adv. Immunol. 38:361 [1986]; Stewart and Weir, J. Clin. Lab. Immunol. 28:103 [1989]; and Lombard et al., supra) and is a potent macrophage activator leading to leukotriene production (Czop, supra), lysosomal enzyme release (Tapper and Sundler, Biochem. J. 306:829 [1995]), arachidonic acid breakdown (Daum and Rohrbach, FEBS 309:110 [1992]), cytokine release (e.g., IL-1, IL-6,TNF-α, IFN-γ) (Ofek et al., Annu. Rev. Microbiol. 49:239 [1995]; and Hashimoto et al., Biol. Pharm. Bull. 20:1006 [1997]), respiratory burst (Berton and Gordon, Immunology 49:705 [1983]) and activation of other pathways that can lead to macrophage mediated cellular toxicity. The co-cultures were maintained for 3 days with macrophages, astrocytes, and a drug treatment. Each group has two components (non-activated macrophages with treatment, and activated macrophages with treatment) for standardization within each group to control for potential variances in drug effects on non-activated culture preparations. After the 3 days of culture, propidium iodide was used to assess cell viability prior to fixation of the cultures with 4% paraformaldehyde. The fixed cultures were stained with antibodies to GFAP to identify astrocytes, ED1 to stain macrophages, and DAPI to label all cell nuclei. For each coverslip, six microscopic fields of view were photographed from a standard grid using a low-power 16× objective. These photographs were scanned into a computer, randomized, and analyzed blindly with NIH Image to count number of live astrocytes, number of live macrophages, cell density, and size of culture cavities. The quantitative data from each measurement group was expressed per field of view relative to the appropriate control group average being standardized to a value of 1. Data was subsequently analyzed with statistical software using analysis of variance (ANOVA) and Fisher's PLSD for multiple comparisons.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cell biology, the neurosciences, medicine, chemistry, and molecular biology or related fields are intended to be within the scope of the following claims.

We claim:

1. A method for treating Alzheimer's disease, comprising administering a therapeutically effective amount of at least one PPARγ agonist to a subject, wherein said PPARγ agonist is selected from the group consisting of troglitazone, ciglitazone, pioglitazone, BRL 49653, and englitazone.

2. The method of claim 1, wherein said subject is selected from the group consisting of subjects identified as being susceptible to Alzheimer's disease and subjects suffering from Alzheimer's disease.

3. The method of claim 1, wherein said therapeutically effective amount of said PPARγ agonist is between 0.1 mg to 100 mg.

4. The method of claim 1, wherein said therapeutically effective amount of said PPARγ agonist comprises approximately 10 mg/kg per day.

5. The method of claim 1, wherein said administering comprises oral administering.

6. A method for treating a central nervous system injury, comprising administering a therapeutically effective amount of at least one PPARγ agonist to a subject suffering from a central nervous system injury, wherein said PPARγ agonist is selected from the group consisting of troglitazone, ciglitazone, pioglitazone, BRL 49653, and englitazone.

7. The method of claim 6, wherein said therapeutically effective amount of said PPARγ agonist is between 0.1 mg to 100 mg.

8. The method of claim 6, wherein said therapeutically effective amount of said PPARγ agonist comprises approximately 10 mg/kg per day.

9. The method of claim 6, wherein said administering step comprises oral administering.

10. The method of claim 6, wherein said central nervous system injury comprises an injury selected from the group consisting of stroke, ischemic damage to said nervous system, and neural trauma.

11. The method of claim 10, wherein said neural trauma comprises damage selected from the group consisting of percussive brain damage, traumatic damage, and spinal cord injury.

12. The method of claim 6, wherein said central nervous system injury comprises multiple sclerosis.

13. The method of claim 6, wherein said central nervous system injury comprises Guillain-Barre syndrome.

14. The method of claim 6, wherein said central nervous system injury comprises acute motor axonal neuropathy.

15. The method of claim 6, wherein said central nervous system injury comprises acute inflammatory demyelinating polyneuropathy.

16. The method of claim 6, wherein said central nervous system injury comprises Fisher syndrome.

17. The method of claim 6, wherein said central nervous system injury comprises HIV/AIDS dementia complex.

18. The method of claim 6, wherein said central nervous system injury comprises meningitis selected from the group consisting of bacterial meningitis and viral meningitis.

* * * * *